United States Patent [19]
Chen et al.

[11] Patent Number: 6,015,926
[45] Date of Patent: Jan. 18, 2000

[54] EFFICIENT ENANTIOSELECTIVE ADDITION REACTION USING AN ORGANOZINC REAGENT

[75] Inventors: Cheng Yi Chen, Colonia; Lushi Tan, Edison; Richard D. Tillyer, Westfield, all of N.J.

[73] Assignee: Merck & Co., Inc., Rahway, N.J.

[21] Appl. No.: 09/075,476

[22] Filed: May 11, 1998

Related U.S. Application Data

[60] Provisional application No. 60/046,713, May 16, 1997, and provisional application No. 60/057,884, Sep. 3, 1997.

[51] Int. Cl.[7] .......................... C07C 211/45; C07D 265/18
[52] U.S. Cl. .......................... 564/442; 564/443; 568/807; 568/812; 568/813; 568/840; 568/843; 544/92
[58] Field of Search ...................................... 564/442, 443; 544/92; 568/807, 812, 813, 840, 843

[56] References Cited

U.S. PATENT DOCUMENTS

| | | | |
|---|---|---|---|
| 5,519,021 | 5/1996 | Young et al. | 514/230.5 |
| 5,633,405 | 5/1997 | Thompson et al. | 514/230.5 |
| 5,663,169 | 9/1997 | Young et al. | 514/230.5 |
| 5,663,467 | 9/1997 | Thompson et al. | 585/359 |
| 5,665,720 | 9/1997 | Young et al. | 514/230.5 |
| 5,698,741 | 12/1997 | Thompson et al. | 564/389 |
| 5,811,423 | 9/1998 | Young et al. | 514/230.5 |

FOREIGN PATENT DOCUMENTS

| | | |
|---|---|---|
| WO 95/20389 | 8/1995 | WIPO . |
| WO 96/37457 | 11/1996 | WIPO . |
| WO 98/30540 | 7/1998 | WIPO . |
| WO 98/33782 | 8/1998 | WIPO . |
| WO 98/34928 | 8/1998 | WIPO . |

OTHER PUBLICATIONS

Soai, K., et al., J. Org. Chem., vol. 56, pp. 4264–4268, 1991.
Soai, K., et al., Chem. Rev., vol. 92, pp. 833–856, 1992.
Noyori, R., et al., Angew. Chem. Int. Ed. Engl., vol. 30, pp. 49–69, 1991.
Bolm, C., et al., Angew. Chem. Int. Ed. Engl., vol. 35(15), pp. 1657–1659, 1995.
Huffman, M., et al., J. Org. Chem., vol. 60, pp. 1590–1594, 1995.
Lutjens, H., et al., Tetrahedron: Aymmetry, vol. 6(11), pp. 2675–2678, 1995.
Thompson, A.S., et al., Tetrahedron Letters, vol. 36(49), pp. 8937–8940, 1995.

*Primary Examiner*—Joseph K. McKane
*Attorney, Agent, or Firm*—Valerie J. Camara; Mark R. Daniel

[57] ABSTRACT

An efficient method for the preparation of key intermediate, in the synthesis of (−)-6-chloro-4-cyclopropylethynyl-4-trifluoromethyl-1,4-dihydro-2H-3,1-benzoxazin-2-one, a reverse transcriptase inhibitor is achieved using a chiral addition reaction to the 4-chloro-2-trifluoromethylketoaniline with an organozinc complex to give the desired alcohol. This instant method has broad applicability in the chiral addition to any prochiral ketone.

23 Claims, No Drawings

EFFICIENT ENANTIOSELECTIVE ADDITION REACTION USING AN ORGANOZINC REAGENT

This application is based on Provisional Application No. 60/046,713 filed May 16, 1997 and based on Provisional Application No. 60/057,884 filed Sep. 3, 1997.

BACKGROUND OF THE INVENTION

A key step in the synthesis of the reverse transcriptase inhibitor, (-)-6-chloro-4-cyclopropylethynyl-4-trifluoromethyl-1,4-dihydro-2H-3,1-benzoxazin-2-one, also known as DMP-266, is the chiral addition to the 2-trifluoromethylcarbonyl-4-chloroaniline using a nucleophile, a chiral additive, a non-chiral additive and an organozinc.

The synthesis of DMP-266 and structurally similar reverse transcriptase inhibitors are disclosed in U.S. Pat. No. 5,519,021 and the corresponding PCT International Patent Application WO 95/20389, which published on Aug. 3, 1995. Additionally, the asymmetric synthesis of an enantiomeric benzoxazinone by a highly enantioselective acetylide addition and cyclization sequence that has been described by Thompson, et al., Tetrahedron Letters 1995, 36, 8937–8940, as well as the PCT publication, WO 96/37457, which published on Nov. 28, 1996.

Additionally, several applications have been filed which disclose various aspects of the synthesis of (-)-6-chloro-4-cyclopropyl-ethynyl-4-trifluoromethyl-1,4-dihydro-2H-3,1-benzoxazin-2-one including: 1) a process for making the chiral alcohol, U.S. Ser. No. 60/035,462, filed Jan. 14, 1997; 2) the chiral additive, U.S. Ser. No. 60/034,926, filed Jan. 10, 1997; 3) the cyclization reaction, U.S. Ser. No. 60/037,059, filed Feb. 12, 1997; and the anti-solvent crystallization procedure, U.S. Ser. No. 60/037,385 filed Feb. 5, 1997 and U.S. Ser. No. 60/042,807 filed Apr. 8, 1997.

The instant invention discloses an efficient method for the chiral addition of cyclopropylacetylene to a ketone of formula:

using a chiral organozinc complex to give an amino alcohol of formula:

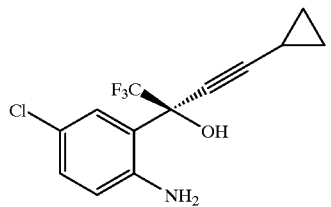

SUMMARY OF THE INVENTION

The instant invention relates to an efficient method for the preparation of a compound of formula I:

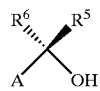

or its enantiomer, wherein

A is:
  (a) $C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, NH($C_1$–$C_6$-alkyl), N($C_1$–$C_6$-alkyl)$_2$, $CONH_2$, CONH($C_1$–$C_6$-alkyl), CON($C_1$–$C_6$-alkyl)$_2$, $NHCONH_2$, NHCONH ($C_1$–$C_6$-alkyl), NHCON($C_1$–$C_6$-alkyl)$_2$, $CO_2$—$C_1$–$C_6$-alkyl, $C_3$–$C_7$-cycloalkyl, or $C_1$–$C_6$-alkoxy;
  (b) phenyl, biphenyl, or naphthyl, unsubstituted or substituted with one to four substituents selected from $R^1$, $R^2$, $R^3$, and $R^4$;

$R^1$, $R^2$, $R^3$, and $R^4$ are independently:
  halo (Cl, Br, F, I), $CF_3$, CN, $NO_2$, $NH_2$, NH($C_1$–$C_6$-alkyl), N($C_1$–$C_6$-alkyl)$_2$, $CONH_2$, CONH($C_1$–$C_6$-alkyl), CON($C_1$–$C_6$-alkyl)$_2$, $NHCONH_2$, NHCONH ($C_1$–$C_6$-alkyl), NHCON($C_1$–$C_6$-alkyl)$_2$, aryl, $CO_2$—$C_1$–$C_6$-alkyl, $C_1$–$C_6$-alkyl, $C_2$–$C_6$-alkenyl, $C_2$–$C_6$-alkynyl, $C_3$–$C_7$-cycloalkyl, or $C_1$–$C_6$-alkoxy, such that $C_1$–$C_6$-alkyl is unsubstituted or substituted with aryl, aryl is defined as phenyl, biphenyl, or naphthyl, unsubstituted or substituted with $C_1$–$C_6$-alkyl, $C_1$–$C_6$-alkoxy, $NO_2$, or halo (Cl, Br, F, I);

$R^5$ is:
  (a) H,
  (b) $C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, NH($C_1$–$C_6$-alkyl), N($C_1$–$C_6$-alkyl)$_2$, $CONH_2$, CONH($C_1$–$C_6$-alkyl), CON($C_1$–$C_6$-alkyl)$_2$, $NHCONH_2$, NHCONH ($C_1$–$C_6$-alkyl), NHCON($C_1$–$C_6$-alkyl)$_2$, $CO_2$—$C_1$–$C_6$-alkyl, $C_3$–$C_7$-cycloalkyl, or $C_1$–$C_6$-alkoxy;
  (c) $C_1$–$C_4$-perfluoroalkyl, $R^6$ is:
  $C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, NH($C_1$–$C_6$-alkyl), N($C_1$–$C_6$-alkyl)$_2$, $CONH_2$, CONH($C_1$–$C_6$-alkyl), CON($C_1$–$C_6$-alkyl)$_2$, $NHCONH_2$, NHCONH ($C_1$–$C_6$-alkyl), NHCON($C_1$–$C_6$-alkyl)$_2$, $CO_2$—$C_1$–$C_6$-alkyl, $C_3$–$C_7$-cycloalkyl or $C_1$–$C_6$-alkoxy;

comprising the steps of:
  a) adding slowly a dialkylzinc in a solvent or neat, to a first chiral additive, or alternatively, to a mixture of a first chiral additive and a second additive, in a solvent under an inert atmosphere at a temperature of about −78° C. to about 50° C. to form a chiral zinc complex or a second additive containing chiral zinc complex;
  b) adding a second additive to a chiral zinc complex, and heating the reaction to about 10° C. to about 70° C. to form a second additive containing chiral zinc complex, where the first chiral additive bears one and only one exchangeable proton, or alternatively, where the first chiral additive bears more than one exchangeable proton, or the second additive was added in step a), then this addition step is skipped;

c) mixing the second additive containing chiral zinc complex with an organometallic reagent of formula, $R^6M$, where M is: Li, Na, K, Zn, $MgX_1$, $CuX_1$, or $B(X_1)_2$; and $X_1$ is Cl, Br, I, F, or $CF_3SO_2$; in a solvent at a temperature range of −20° C. to about 60° C. to form a chiral organozinc complex; and d) mixing a ketone of formula:

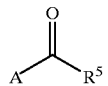

optionally dissolved in a solvent with the solution of the chiral organozinc complex under an inert atmosphere at a temperature of about −20° C. to about 60° C. for about 1 hour to about 72 hours.

DETAILED DESCRIPTION OF THE INVENTION

The instant invention relates to an efficient method for the preparation of a compound of formula I:

or its enantiomer, wherein

A is:
(a) $C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH ($C_1$–$C_6$-alkyl), $NHCON(C_1$–$C_6$-alkyl)$_2$, $CO_2$— $C_1$–$C_6$-alkyl, $C_3$–$C_7$-cycloalkyl, or $C_1$–$C_6$-alkoxy;

(b) phenyl, biphenyl, or naphthyl, unsubstituted or substituted with one to four substituents selected from $R^1$, $R^2$, $R^3$, and $R^4$;

$R^1$, $R^2$, $R^3$, and $R^4$ are independently:
halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH ($C_1$–$C_6$-alkyl), $NHCON(C_1$–$C_6$-alkyl)$_2$, aryl, $CO_2$— $C_1$–$C_6$-alkyl, $C_1$–$C_6$-alkyl, $C_2$–$C_6$-alkenyl, $C_2$–$C_6$-alkynyl, $C_3$–$C_7$-cycloalkyl, or $C_1$–$C_6$-alkoxy, such that $C_1$–$C_6$-alkyl is unsubstituted or substituted with aryl, aryl is defined as phenyl, biphenyl, or naphthyl, unsubstituted or substituted with $C_1$–$C_6$-alkyl, $C_1$–$C_6$-alkoxy, $NO_2$, or halo (Cl, Br, F, I);

$R^5$ is:
(a) H,
(b) $C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH ($C_1$–$C_6$-alkyl), $NHCON(C_1$–$C_6$-alkyl)$_2$, $CO_2$— $C_1$–$C_6$-alkyl, $C_3$–$C_7$-cycloalkyl, or $C_1$–$C_6$-alkoxy;
(c) $C_1$–$C_4$-perfluoroalkyl, $R^6$ is:
$C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH (C1–C6-alkyl), $NHCON(C_1$–$C_6$-alkyl)$_2$, $CO_2$— $C_1$–$C_6$-alkyl, $C_3$–$C_7$-cycloalkyl or $C_1$–$C_6$-alkoxy;

comprising the steps of:
a) adding slowly a dialkylzinc in a solvent or neat, to a first chiral additive, or alternatively, to a mixture of a first chiral additive and a second additive, in a solvent under an inert atmosphere at a temperature of about −78° C. to about 50° C. to form a chiral zinc complex or a second additive containing chiral zinc complex;

b) adding a second additive to a chiral zinc complex, and heating the reaction to about 10° C. to about 70° C. to form a second additive containing chiral zinc complex, where the first chiral additive bears one and only one exchangeable proton, or alternatively, where the first chiral additive bears more than one exchangeable proton, or the second additive was added in step a), then this addition step is skipped;

c) mixing the second additive containing chiral zinc complex with an organometallic reagent of formula, $R^6M$, where M is: Li, Na, K, Zn, $MgX_1$, $CuX_1$, or $B(X_1)_2$; and $X_1$ is Cl, Br, I, F, or $CF_3SO_2$; in a solvent at a temperature range of −20° C. to about 60° C. to form a chiral organozinc complex; and d) mixing a ketone of formula:

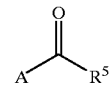

optionally dissolved in a solvent with the solution of the chiral organozinc complex under an inert atmosphere at a temperature of about −20° C. to about 60° C. for about 1 hour to about 72 hours.

An embodiment of the instant invention relates to an efficient method for the preparation of a compound of formula I:

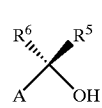

or its enantiomer, wherein

A is:
(a) $C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH ($C_1$–$C_6$-alkyl), $NHCON(C_1$–$C_6$-alkyl)$_2$, $CO_2$— $C_1$–$C_6$-alkyl, $C_3$–$C_7$-cycloalkyl, or $C_1$–$C_6$-alkoxy;

(b) phenyl, biphenyl, or naphthyl, unsubstituted or substituted with one to four substituents selected from $R^1$, $R^2$, $R^3$, and $R^4$;

$R^1$, $R^2$, $R^3$, and $R^4$ are independently:
halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH ($C_1$–$C_6$-alkyl), $NHCON(C_1$–$C_6$-alkyl)$_2$, aryl, $CO_2$—

$C_1$–$C_6$-alkyl, $C_1$–$C_6$-alkyl, $C_2$–$C_6$-alkenyl, $C_2$–$C_6$-alkynyl, $C_3$–$C_7$-cycloalkyl, or $C_1$–$C_6$-alkoxy, such that $C_1$–$C_6$-alkyl is unsubstituted or substituted with aryl, aryl is defined as phenyl, biphenyl, or naphthyl, unsubstituted or substituted with $C_1$–$C_6$-alkyl, $C_1$–$C_6$-alkoxy, $NO_2$, or halo (Cl, Br, F, I);

$R^5$ is:
(a) H,
(b) $C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH($C_1$–$C_6$-alkyl), $NHCON(C_1$–$C_6$-alkyl)$_2$, $CO_2$—$C_1$–$C_6$-alkyl, $C_3$–$C_7$-cycloalkyl, or $C_1$–$C_6$-alkoxy;
(c) $C_1$–$C_4$-perfluoroalkyl, $R^6$ is:
$C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH($C_1$–$C_6$-alkyl), $NHCON(C_1$–$C_6$-alkyl)$_2$, $CO_2$—$C_1$–$C_6$-alkyl, $C_3$–$C_7$-cycloalkyl or $C_1$–$C_6$-alkoxy;

comprising the steps of:
a) adding slowly a dialkylzinc in a solvent or neat, to a first chiral additive in a solvent under an inert atmosphere at a temperature of about −78° C. to about 50° C. to form a chiral zinc complex;
b) adding a second additive to a chiral zinc complex, and heating the reaction to about 10° C. to about 70° C. to form a second additive containing chiral zinc complex, where the first chiral additive bears one and only one exchangeable proton;
c) mixing the second additive containing chiral zinc complex with an organometallic reagent of formula, $R^6M$, where M is: Li, Na, K, Zn, $MgX_1$, $CuX_1$, or $B(X_1)_2$; and $X_1$ is Cl, Br, I, F, or $CF_3SO_2$; in a solvent at a temperature range of −20° C. to about 60° C. to form a chiral organozinc complex; and
d) mixing a ketone of formula:

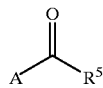

optionally dissolved in a solvent with the solution of the chiral organozinc complex under an inert atmosphere at a temperature of about −20° C. to about 60° C. for about 1 hour to about 72 hours.

Another embodiment of the instant invention relates to an efficient method for the preparation of a compound of formula I:

I or its enantiomer, wherein
A is:
(a) $C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH($C_1$–$C_6$-alkyl), $NHCON(C_1$–$C_6$-alkyl)$_2$, $CO_2$—$C_1$–$C_6$-alkyl, $C_3$–$C_7$-cycloalkyl, or $C_1$–$C_6$-alkoxy;
(b) phenyl, biphenyl, or naphthyl, unsubstituted or substituted with one to four substituents selected from $R^1$, $R^2$, $R^3$, and $R^4$;

$R^1$, $R^2$, $R^3$, and $R^4$ are independently:
halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH($C_1$–$C_6$-alkyl), $NHCON(C_1$–$C_6$-alkyl)$_2$, aryl, $CO_2$—$C_1$–$C_6$-alkyl, $C_1$–$C_6$-alkyl, $C_2$–$C_6$-alkenyl, $C_2$–$C_6$-alkynyl, $C_3$–$C_7$-cycloalkyl, or $C_1$–$C_6$-alkoxy, such that $C_1$–$C_6$-alkyl is unsubstituted or substituted with aryl, aryl is defined as phenyl, biphenyl, or naphthyl, unsubstituted or substituted with $C_1$–$C_6$-alkyl, $C_1$–$C_6$-alkoxy, $NO_2$, or halo (Cl, Br, F, I);

$R^5$ is:
(a) H,
(b) $C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH($C_1$–$C_6$-alkyl), $NHCON(C_1$–$C_6$-alkyl)$_2$, $CO_2$—$C_1$–$C_6$-alkyl, $C_3$–$C_7$-cycloalkyl, or $C_1$–$C_6$-alkoxy;
(c) $C_1$–$C_4$-perfluoroalkyl, $R^6$ is:
$C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, NHCONH($C_1$–$C_6$-alkyl), $NHCON(C_1$–$C_6$-alkyl)$_2$, $CO_2$—$C_1$–$C_6$-alkyl, $C_3$–$C_7$-cycloalkyl or $C_1$–$C_6$-alkoxy;

comprising the steps of:
a) adding slowly a dialkylzinc in a solvent or neat, to a mixture of a first chiral additive and a second additive, in a solvent under an inert atmosphere at a temperature of about −78° C. to about 50° C. to form a second additive containing chiral zinc complex;
b) mixing the second additive containing chiral zinc complex with an organometallic reagent of formula, $R^6M$, where M is: Li, Na, K, Zn, $MgX_1$, $CuX_1$, or $B(X_1)_2$; and $X_1$ is Cl, Br, I, F, or $CF_3SO_2$; in a solvent at a temperature range of −20° C. to about 60° C. to form a chiral organozinc complex; and
c) mixing a ketone of formula:

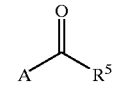

optionally dissolved in a solvent with the solution of the chiral organozinc complex under an inert atmosphere at a temperature of about −20° C. to about 60° C. for about 1 hour to about 72 hours.

The processes as recited above, wherein the first chiral additive has the formula:

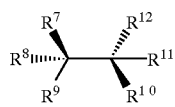

or its enantiomer or diastereomer, and the substituents are defined as:

$R^9$ and $R^{10}$ are independently:
OH, $NH_2$, $NHR^{17}$, $N(R^{17})_2$, or

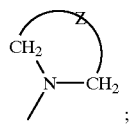

$R^7$, $R^8$, $R^{11}$ and $R^{12}$ are independently:
(a) H,
(b) $CF_3$,
(c) CN,
(d) $CONH_2$,
(e) $CONH(C_1-C_6\text{-alkyl})$,
(f) $CON(C_1-C_6\text{-alkyl})_2$,
(g) $CO_2-C_1-C_6\text{-alkyl}$,
(h) $C_3-C_7$-cycloalkyl,
(i) $C_1-C_6$-alkyl, $C_2-C_6$-alkenyl, or $C_2-C_6$-alkynyl, unsubstituted or mono- or di-substituted with a substituent selected from the group consisting of: halo (Cl, Br, F, I), $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, $CON(C_1-C_6\text{-alkyl})_2$, $NHCONH_2$, NHCONH $(C_1-C_6\text{-alkyl})$, $NHCON(C_1-C_6\text{-alkyl})_2$, $CO_2-$ $C_1-C_6$-alkyl, $C_3-C_7$-cycloalkyl, $C_1-C_6$-alkoxy;
(j) $R^7$ and $R^8$ or $R^{11}$ and $R^{12}$ taken together can represent =O, forming a ketone, amide, acid or ester group;
(k)

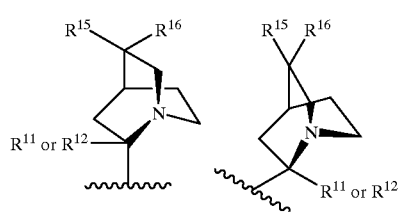

such that one and only one of $R^7$, $R^8$, $R^{11}$, or $R^{12}$ can bear this definition,
except that at least one of the two carbons bearing $R^7$, $R^8$, $R^9$, $R^{10}$, $R^{11}$ and $R^{12}$ is a chiral center;

$R^9$ taken together with either $R^{11}$ or $R^{12}$ can represent:

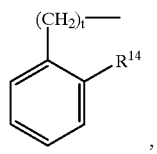

such that the other of $R^{11}$ or $R^{12}$ is hydrogen; or $R^{10}$ taken together with either $R^7$ or $R^8$ can represent:

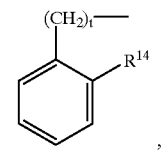

such that the other of $R^7$ or $R^8$ is hydrogen;

$R^{13}$ is: H, $C_1-C_6$-alkyl, or phenyl;

$R^{14}$ is: H, except that $R^7$ or $R^8$ and $R^{14}$ taken together can represent a carbon carbon bond, when t is 1 or 2 and $R^{11}$ or $R^{12}$ represents

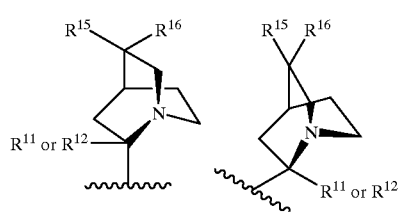

or $R^7$ or $R^8$ and $R^{14}$ taken together can represent $-(CH_2)_s-$, when t is 0 and $R^{11}$ or $R^{12}$ represents

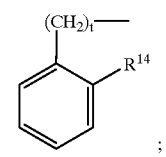

$R^{15}$ or $R^{16}$ is: $C_1-C_6$-alkyl, $C_2-C_6$-alkenyl, or $C_2-C_6$-alkynyl, unsubstituted or mono- or di-substituted with a substituent selected from the group consisting of: halo (Cl, Br, F, I), $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, CON $(C_1-C_6\text{-alkyl})_2$, $NHCONH_2$, $NHCONH(C_1-C_6\text{-alkyl})$, $NHCON(C_1-C_6\text{-alkyl})_2$, $CO_2-C_1-C_6$-alkyl, $C_3-C_7$-cycloalkyl, $C_1-C_6$-alkoxy; such that the other of $R^{15}$ and $R^{16}$ is hydrogen;

$R^{17}$ is: $C_1-C_6$-alkyl, unsubstituted or substituted with aryl, or aryl, wherein aryl is defined as phenyl or naphthyl;

Z represents:

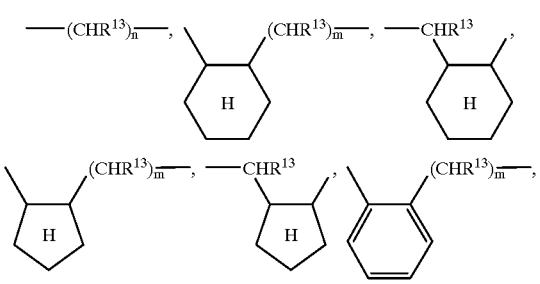

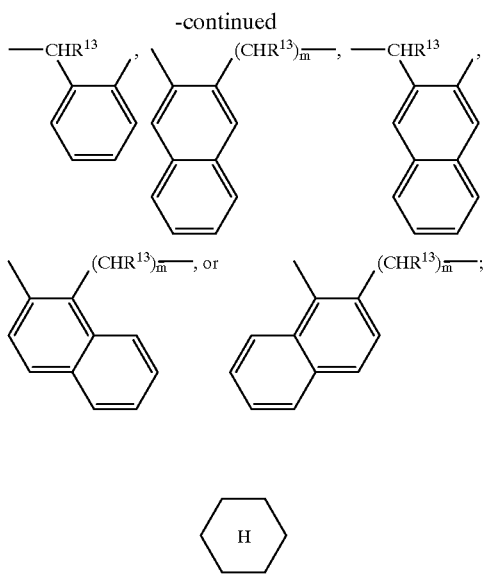

represents a six-membered ring, unsaturated or saturated, optionally substituted with one or two heteroatoms selected from N, O, or S, optionally substituted with $C_1$–$C_6$-alkyl;

represents: a five-membered ring, unsaturated or saturated, optionally substituted with one or two heteroatoms selected from N, O, or S, optionally substituted with $C_1$–$C_6$-alkyl;

n is 1, 2, or 3;

m is 0, or 1;

t is 0, 1, or 2; and s is 1 or 2.

The representative examples of the first chiral additive are: (1R, 2S)-N-pyrrolidinyl norephedrine (also referred to in the Chemicial Abstract Registry as [R-(R*,S*)]-β-methyl-α-phenyl-1-pyrrolidine-ethanol), N-methylephedrine, ephedrine, N,N-dibenzylnorephedrine, norephedrine, diethyl tartrate, pyrrolidine-methanol, (1R,2R)-pseudoephedrine, cinchonine, (1S,2S)-N-methylpseudoephedrine.

The dialkylzinc is defined as a $[C_1$–$C_6$-alkyl$]_2$Zn, and preferably, dimethylzinc or diethylzinc. In the examples presented, the dimethylzinc or diethylzinc was purchased as a toluene or hexane solution, however, the reagent can be utilized neat.

The second additive is defined as an alcohol, ROH, thiol, RSH, carboxylic acid, $RCO_2H$, sulfonic acid, $RSO_3H$, a hydrogen halide, HX, a carboxamide, $RCONH_2$, and an aniline, aryl$NH_2$ and R is $C_1$–$C_6$-alkyl, $C_2$–$C_6$-alkenyl, $C_2$–$C_6$-alkynyl, aryl, where aryl is defined as phenyl or naphthyl, and heteroaryl, where heteroaryl is defined as a 5 or 6-membered aromatic ring substituted with one or two heteroatoms selected from O, S, N, and each of which is unsubstituted or substituted with one, two or three substituents selected from the group consisting of: $NO_2$, Cl, Br, I, F, $CF_3$, $C_1$–$C_6$-alkyl, $C_1$–$C_6$-alkoxy, and $N[C_1$–$C_6$-alkyl$]_2$; and X is Cl, Br, I, or F. Preferred second additives are defined as MeOH, t-BuOH, $(CH_3)_3CCH_2OH$, $(CH_3)_3CCH(CH_3)OH$, $Ph_3COH$, $Cl_3CCH_2OH$, $F_3CCH_2OH$, $CH_2=CHCH_2OH$, $PhCH_2OH$, $(CH_3)_2NCH_2CH_2OH$, 4-$NO_2$-phenol, $CH_3CO_2H$, $CF_3CO_2H$, and $(CH_3)CCO_2H$. The second additive is optional, when the first chiral additive bears at least two exchangeable protons. For example, a first chiral additive such as ephedrine, norephedrine, pseudoephedrine, diethyl tartrate, or those first chiral additives where $R^9$ and $R^{10}$ independently represent OH and $NH_2$; may be used without the addition of a second additive. Also with the scope of the definition of a second additive is the fact that this additive may also be chiral.

The solvent is defined as a polar or non-polar aprotic solvent, or mixtures of these solvents, such as tetrahydrofuran (THF), benzene, chlorobenzene, o-, m-, p-dichlorobenzene, dichloromethane, toluene, hexane, cyclohexane, pentane, methyl t-butyl ether (MTBE), diethyl ether, N-methylpyrrolidine (NMP), or mixtures of said solvents. Preferably the solvent(s) is(are) selected from the group consisting of teterahydrofuran, toluene and hexane.

An embodiment of the invention discloses a process for the preparation of an amino alcohol of formula:

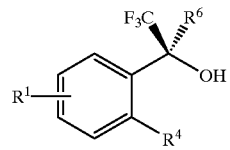

wherein:

$R^1$ is:
halo (Cl, Br, F, I), $CF_3$, CN, $NO_2$, $NH_2$, NH($C_1$–$C_6$-alkyl), N($C_1$–$C_6$-alkyl$)_2$, $CONH_2$, CONH($C_1$–$C_6$-alkyl), CON($C_1$–$C_6$-alkyl$)_2$, $NHCONH_2$, NHCONH ($C_1$–$C_6$-alkyl), NHCON($C_1$–$C_6$-alkyl$)_2$, aryl, $CO_2$—$C_1$–$C_6$-alkyl, $C_1$–$C_6$-alkyl, $C_2$–$C_6$-alkenyl, $C_2$–$C_6$-alkynyl, $C_3$–$C_7$-cycloalkyl, or $C_1$–$C_6$-alkoxy, such that $C_1$–$C_6$-alkyl is unsubstituted or substituted with aryl, aryl is defined as phenyl, biphenyl, or naphthyl, unsubstituted or substituted with $C_1$–$C_6$-alkyl, $C_1$–$C_6$-alkoxy, $NO_2$, or halo (Cl, Br, F, I);

$R^4$ is:
$NH_2$, or NH($C_1$–$C_6$-alkyl), such that $C_1$–$C_6$-alkyl is unsubstituted or substituted with aryl, aryl is defined as phenyl or naphthyl, unsubstituted or substituted with $C_1$–$C_6$-alkyl, $C_1$–$C_6$-alkoxy, $NO_2$, or halo (Cl, Br, F, I);

$R^6$ is:
$C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, NH($C_1$–$C_6$-alkyl), N($C_1$–$C_6$-alkyl$)_2$, $CONH_2$, CONH($C_1$–$C_6$-alkyl), CON($C_1$–$C_6$-alkyl$)_2$, $NHCONH_2$, NHCONH ($C_1$–$C_6$-alkyl), NHCON($C_1$–$C_6$-alkyl$)_2$, $CO_2$—$C_1$–$C_6$-alkyl, $C_3$–$C_7$-cycloalkyl, or $C_1$–$C_6$-alkoxy;

comprising the steps of:
a) adding slowly a dialkylzinc in a solvent or neat, to a first chiral additive, or alternatively, to a mixture of a first chiral additive and a second additive, in a solvent under an inert atmosphere at a temperature of about −78° C. to about 50° C. to form a chiral zinc complex or a second additive containing chiral zinc complex;

b) adding a second additive to a chiral zinc complex, and heating the reaction to about 10° C. to about 70° C. to form a second additive containing chiral zinc complex, where the first chiral additive bears one and only one exchangeable proton, or alternatively, where the first chiral additive bears more than one exchangeable proton, or the second additive was added in step a), then this addition step is skipped;

c) mixing the second additive containing chiral zinc complex with an organometallic reagent of formula, $R^6M$, wherein M represents: Na, K, Li, $MgX_1$, $ZnX_1$, $CuX_1$, or $B(X_1)_2$; and $X_1$ is Cl, Br, I, F, or $CF_3SO_2$; in a solvent to form a chiral organozinc complex; and d) mixing a ketone of formula:

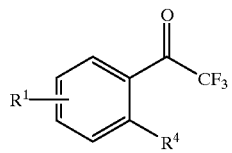

optionally dissolved in a solvent with the solution of the chiral organozinc complex under an inert atmosphere at a temperature of about 0° C. to about 60° C. for about 1 hour to about 72 hours.

The process as recited above, wherein the first chiral additive has the formula:

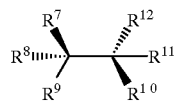

or its enantiomer or diastereomer, and the substituents are defined as:

$R^9$ and $R^{10}$ are independently:
OH, $NH_2$, $NHR^{17}$, $N(R^{17})_2$, or

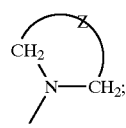

$R^7$, $R^8$, $R^{11}$ and $R^{12}$ are independently:
(a) H,
(b) $CF_3$,
(c) CN,
(d) $CONH_2$,
(e) $CONH(C_1-C_6\text{-alkyl})$,
(f) $CON(C_1-C_6\text{-alkyl})_2$,
(g) $CO_2-C_1-C_6\text{-alkyl}$,
(h) $C_3-C_7\text{-cycloalkyl}$,
(i) $C_1-C_6\text{-alkyl}$, $C_2-C_6\text{-alkenyl}$, or $C_2-C_6\text{-alkynyl}$, unsubstituted or mono- or di-substituted with a substituent selected from the group consisting of: halo (Cl, Br, F, I), $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, $CON(C_1-C_6\text{-alkyl})_2$, $NHCONH_2$, $NHCONH(C_1-C_6\text{-alkyl})$, $NHCON(C_1-C_6\text{-alkyl})_2$, $CO_2-C_1-C_6\text{-alkyl}$, $C_3-C_7\text{-cycloalkyl}$, $C_1-C_6\text{-alkoxy}$;
(j) $R^7$ and $R^8$ or $R^{11}$ and $R^{12}$ taken together can represent =O, forming a ketone, amide, acid or ester group;

(k)

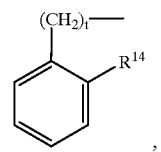

such that one and only one of $R^7$, $R^8$, $R^{11}$, or $R^{12}$ can bear this definition, except that at least one of the two carbons bearing $R^7$, $R^8$, $R^9$, $R^{10}$, $R^{11}$ and $R^{12}$ is a chiral center;

$R^9$ taken together with either $R^{11}$ or $R^{12}$ can represent:

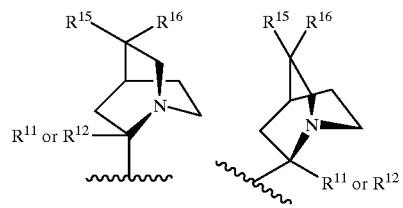

such that the other of $R^{11}$ or $R^{12}$ is hydrogen; or
$R^{10}$ taken together with either $R^7$ or $R^8$ can represent:

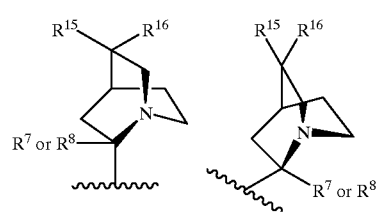

such that the other of $R^7$ or $R^8$ is hydrogen;
$R^{13}$ is: H, $C_1-C_6\text{-alkyl}$, or phenyl;
$R^{14}$ is: H, except that $R^7$ or $R^8$ and $R^{14}$ taken together can represent a carbon carbon bond, when t is 1 or 2 and $R^{11}$ or $R^{12}$ represents

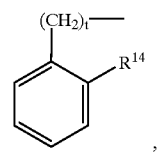

or
$R^7$ or $R^8$ and $R^{14}$ taken together can represent —$(CH_2)_s$—, when t is 0 and $R^{11}$ or $R^{12}$ represents

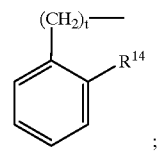

$R^{15}$ or $R^{16}$ is: $C_1-C_6\text{-alkyl}$, $C_2-C_6\text{-alkenyl}$, or $C_2-C_6$-alkynyl, unsubstituted or mono- or di-substituted with a substituent selected from the group consisting of: halo (Cl, Br, F, I), CF$_3$, CN, NO$_2$, NH$_2$, NH(C$_1$–C$_6$-alkyl), N(C$_1$–C$_6$-alkyl)$_2$, CONH$_2$, CONH(C$_1$–C$_6$-alkyl), CON(C$_1$–C$_6$-alkyl)$_2$, NHCONH$_2$, NHCONH(C$_1$–C$_6$-alkyl), NHCON(C$_1$–C$_6$-alkyl)$_2$, CO$_2$—C$_1$–C$_6$-alkyl, C$_3$–C$_7$-cycloalkyl, C$_1$–C$_6$-alkoxy; such that the other of R$^{15}$ and R$^{16}$ is hydrogen;

R$^{17}$ is: C$_1$–C$_6$-alkyl, unsubstituted or substituted with aryl, or aryl, wherein aryl is defined as phenyl or naphthyl;

Z represents:

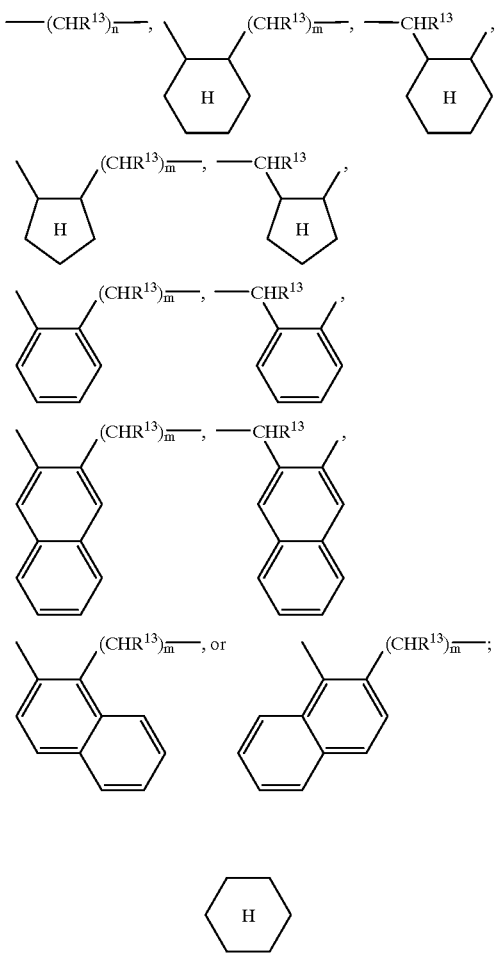

represents a six-membered ring, unsaturated or saturated, optionally substituted with one or two heteroatoms selected from N, O, or S, optionally substituted with C$_1$–C$_6$-alkyl;

represents: a five-membered ring, unsaturated or saturated, optionally substituted with one or two heteroatoms selected from N, O, or S, optionally substituted with C$_1$–C$_6$-alkyl;

n is 1, 2, or 3;
m is 0, or 1;
t is 0, 1, or 2; and
s is 1 or 2.

The process as recited above, wherein dialkylzinc is defined as [C$_1$–C$_6$-alkyl]$_2$Zn.

The process as recited above, wherein the second additive is defined as: ROH, RSH, RCO$_2$H, RSO$_3$H, HX, RCONH$_2$, or ArNH$_2$; wherein R is C$_1$–C$_6$-alkyl, Ar, heteroaryl, and CF$_3$, and Ar is aryl, which is defined as phenyl or naphthyl, unsubstituted or substituted with NO$_2$, Cl, Br, I, F, CF$_3$, C$_1$–C$_6$-alkyl, C$_1$–C$_6$-alkoxy; and X is Cl, Br, I, or F.

The process as recited above, wherein the solvent is defined as a polar or non-polar aprotic solvent.

The process as recited above, wherein the first chiral additive is selected from the group consisting of: (1R, 2S)-N-pyrrolidinyl norephedrine, N-methylephedrine, ephedrine, N,N-dibenzylnorephedrine, norephedrine, diethyl tartrate, pyrrolidine-methanol, (1R,2R)-pseudoephedrine, cinchonine, (1S,2S)-N-methylpseudoephedrine.

The process as recited above, wherein the dialkylzinc is diethylzinc or dimethylzinc.

The process as recited above, wherein the second additive is selected from the group consisting of: MeOH, t-BuOH, (CH$_3$)$_3$CCH$_2$OH, (CH$_3$)$_3$CCH(CH$_3$)OH, Ph$_3$COH, Cl$_3$CCH$_2$OH, F$_3$CCH$_2$OH, CH$_2$=CHCH$_2$OH, PhCH$_2$OH, (CH$_3$)$_2$NCH$_2$CH$_2$OH, 4-NO$_2$-phenol, CH$_3$CO$_2$H, CF$_3$CO$_2$H, and (CH$_3$)CCO$_2$H.

The solvent is defined as a polar or non-polar aprotic solvent, or mixtures of these solvents, such as tetrahydrofuran (THF), benzene, chlorobenzene, o-, m-, p-dichlorobenzene, dichloromethane, toluene, hexane, cyclohexane, pentane, methyl t-butyl ether (MTBE), diethyl ether, N-methylpyrrolidine (NMP), or mixtures of said solvents. Preferably the solvent(s) is(are) selected from the group consisting of teterahydrofuran, toluene and hexane.

The process as recited above, wherein the organometallic reagent, R$^6$M, and R$^6$ represents C$_2$–C$_6$-alkynyl; M represents: Li, or MgX$_1$; and X$_1$ represents: Cl, Br, I, F, or CF$_3$SO$_2$.

A further embodiment of the invention is the process for the preparation of an amino alcohol of formula:

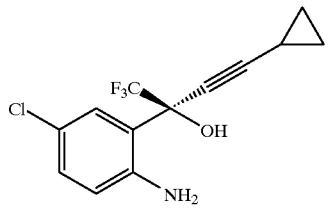

comprising the steps of:

a) adding slowly dimethylzinc or diethylzinc in toluene or neat to (1R, 2S)-N-pyrrolidinyl norephedrine in tetrahydrofuran under a nitrogen atmosphere at a temperature of about –20° C. to about 0° C. to form a chiral zinc complex;

b) adding an alcohol, where the alcohol is neopentyl alcohol or 2,2,2-trifluoroethanol, to the chiral zinc complex and heating to form an alcohol-containing chiral zinc complex;

c) mixing the alcohol-containing chiral zinc complex with

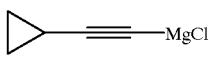

in tetrahydrofuran to form a chiral organozinc complex; and
d) mixing a ketone of formula:

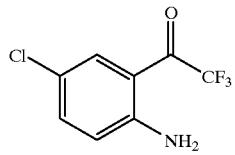

with the solution of the chiral organozinc complex under an inert atmosphere at a temperature of about 0° C. to about 20° C. for about 2 hours to about 48 hours to give the amino alcohol.

A further embodiment of the invention is the process for the preparation of an amino alcohol of formula:

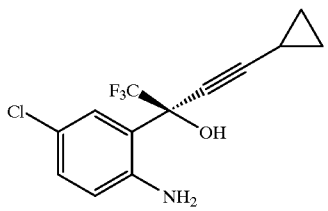

comprising the steps of:
a) adding slowly dimethylzinc or diethylzinc in toluene or neat to (1R, 2S)-N-pyrrolidinyl norephedrine and an alcohol, where the alcohol is neopentyl alcohol or 2,2,2-trifluoroethanol, in tetrahydrofuran under a nitrogen atmosphere at a temperature of about −20° C. to about 0° C. to form an alcohol-containing chiral zinc complex;
b) mixing the alcohol-containing chiral zinc complex with

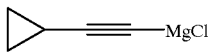

in tetrahydrofuran to form a chiral organozinc complex; and
c) mixing a ketone of formula:

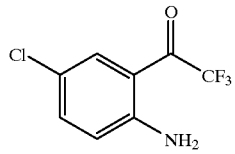

with the solution of the chiral organozinc complex under an inert atmosphere at a temperature of about 0° C. to about 20° C. for about 2 hours to about 48 hours to give the amino alcohol.

The term inert atmosphere is understood to be an atmosphere of argon or nitrogen, preferably nitrogen. Ambient temperature is understood to represent a temperature range of from 20° C. to about 35° C.

The compounds of the present invention have asymmetric centers and this invention includes all of the optical isomers and mixtures thereof.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkenyl and Alkynyl" is intended to include hydrocarbon chains of a specified number of carbon atoms of either a straight- or branched-configuration and at least one double or triple bond, which may occur at any point along the chain. Examples of "alkenyl" include ethenyl, propenyl, butenyl, pentenyl, dimethyl pentenyl, and the like, and includes E and Z forms, where applicable. Examples of "alkynyl" include ethynyl, propynyl, butynyl, pentynyl, and dimethyl pentynyl. "Halogen", as used herein, means fluoro, chloro, bromo and iodo.

The term "aryl" is defined as a phenyl, biphenyl, or naphthyl ring which is optionally substituted with the substituents listed above at any available carbon atoms. The aryl may also be substituted with a fused 5-, 6-, or 7-membered ring containing one or two oxygens and the remaining ring atoms being carbon, the fused 5-, 6-, or 7-ring being selected from the group consisting of: dioxolanyl, dihydrofuranyl, dihydropyranyl, and dioxanyl.

The term "heteroaryl" as utilized herein is intended to include the following a 5 or 6-membered aromatic ring substituted with one or two heteroatoms selected from O, S, N, and is unsubstituted or substituted with one, two or three substituents selected from the group consisting of: Br, Cl, F, I, ($C_1$–$C_6$)-alkoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_{1-C_6}$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

Scheme 1 outlines the key steps in the synthesis of (−)-6-chloro-4-cyclopropylethynyl-4-trifluoromethyl-1,4-dihydro-2H-3,1-benzoxazin-2-one (DMP-266). The chiral addition step allows for the enantioselective addition of the cyclopropylacetylide across the trifluoromethylketone of 1. The p-methoxybenzyl (PMB)-protected amino alcohol, 2, produced is then deprotected to give the amino alcohol, 3. The amino alcohol is then cyclized using a chloroformate and base to give DMP-266.

SCHEME 1

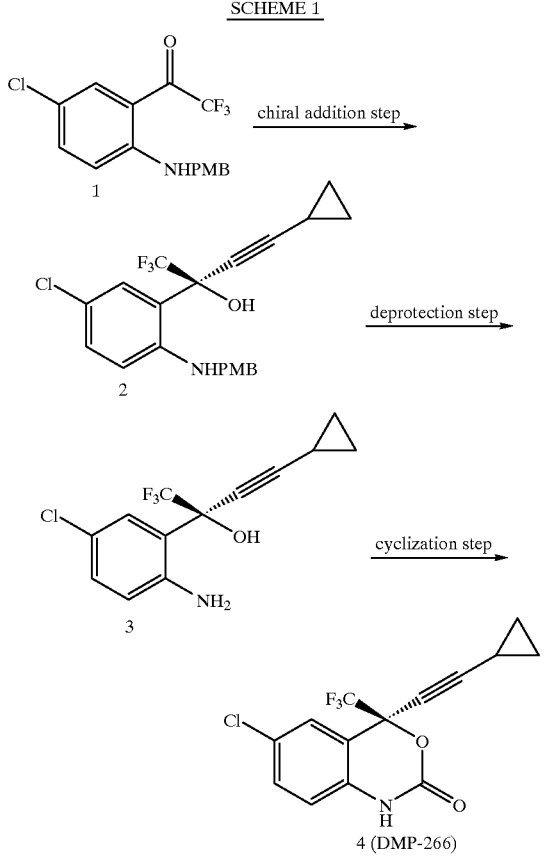

Scheme 2 outlines the preparation of DMP-266 using the the process of the present invention which is a chiral addition reaction. The new chiral addition reaction allows for the elimination of the protection-deprotection sequence as outlined in Scheme 1.

SCHEME 2

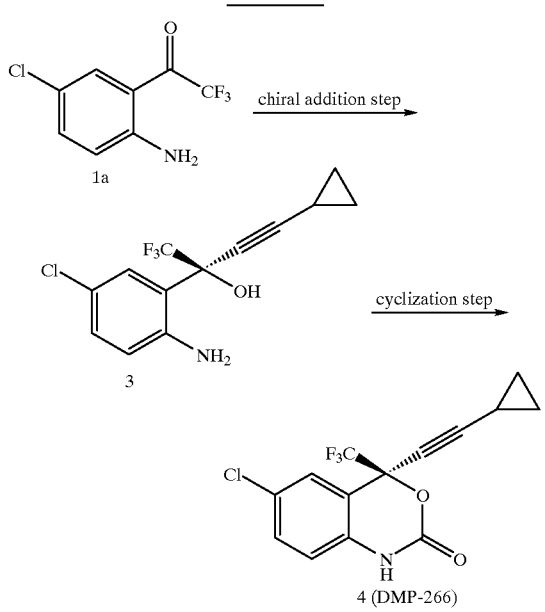

Scheme 3, reaction I describes the process of the instant invention as it relates to the synthesis of the chiral intermediate used in the preparation of DMP-266. This reaction has been demonstrated to work using about 1.2 equivalents of cyclopropylacetylene and chiral additive, much lesss than the prior methods. The numerous chiral additives have been run and give high yields with a commerically available chiral ligand, such as N-methyl ephedrine and N-pyrrolidinyl norephedrine. The general chiral addition reaction is noted in reaction II of this scheme. This process provides an efficient method for the introduction of a chiral alcohol of the desired configuration when the appropriate chiral organozinc complex is formed.

The instant invention discloses a method for the formation of a chiral organozinc complex which contains the nucleophile of choice, $R^6M$. This reagent which is generated in situ is then reacted with a prochiral ketone to form a chiral alcohol.

Preparation of the alcohol 3, required the use of about 1.0 to about 1.5 equivalents of the chiral additive and the nucleophile; or preferably about 1.2 equivalents of the chiral additive and about 1.0 equivalent of the nucleophile.

The reaction can be run at a temperature of about $-78°$ C. to about $70°$ C., and preferably at a temperature of about $-20°$ C. to about $60°$ C., as opposed to the low temperature conditions ($-65°$ C.) required by the prior method. The dialkylzinc is typically added at a temperature of about $-20°$ C. to about $0°$ C. The second additive is typically added at about ambient temperature, the mixture is then heated to about $60°$ C. to effect the formation of the chiral organozinc complex. The organometallic reagent ($R^6M$) is added to the chiral organozinc complex at about room temperature. To this chiral nucleophile-organozinc complex is added the prochiral ketone at about $0°$ C. to about $20°$ C.

The formation of the chiral organozinc complex can be done by the slow addition of dialkylzinc to a mixture of the first chiral additive and the second additive, or alternatively by the slow addition of dialkylzinc to of the first chiral additive, and then adding the second additive to a solution of a chiral zinc complex.

A preferred embodiment of the process of the instant invention involves the slow addition of a solution of the dialkylzinc to a solution containing the chiral additive and second additive so as to maintain the reaction temperature at between $0°$ C. and $30°$ C. After about one hour an organometalic reagent, such as chloromagnesium cyclopropylacetylide, is prepared and added to the chiral organozinc complex. Then, the ketoaniline is added at about $-10°$ C. to this chiral nucleophile-organozinc complex solution. The reaction is stirred for about 35 hours at about $0°$ C. to about $-10°$ C., warmed to room temperature, stirred for about 3 hours, and then quenched with a base.

Additionally, this method has been demonstrated to provide a catalytic method for making the desired chiral alcohol, where a catalytic amount of the chiral additive is utilized.

SCHEME 3

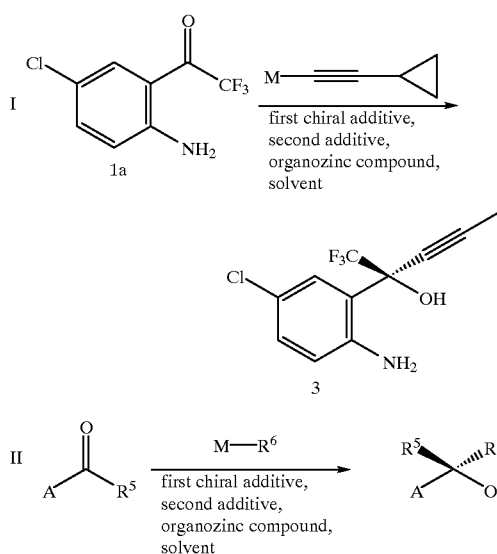

The cyclization of the amino alcohol, 3 to produce the 1,4-dihydro-2H-3,1-benzoxazin-2-one, 4 is outlined in Scheme 4 below. The reaction can be carried out as a one-step process, or alternatively a two step process with the potential isolation of the intermediate carbamate, 5 depending upon the chloroformate utilized. It has been demonstrated that the aryl chloroformates form less stable carbamates such that when they are treated with aqueous base they cyclize to the product, in a one-step process. The alkyl chloroformate, alternatively, provides an alkyl carbamate, a key intermediate capable of being isolated and purified prior to carrying out the cyclization step. Based upon the stability of the alkyl carbamates, a viable two step process for the preparation of DMP-266 has been developed which comprises the formation of the alkyl carbamate intermediate, 5 followed by the cyclization of the carbamate to give the desired product, 4. Additionally, it has been demonstrate that phosgene can also be used.

SCHEME 4

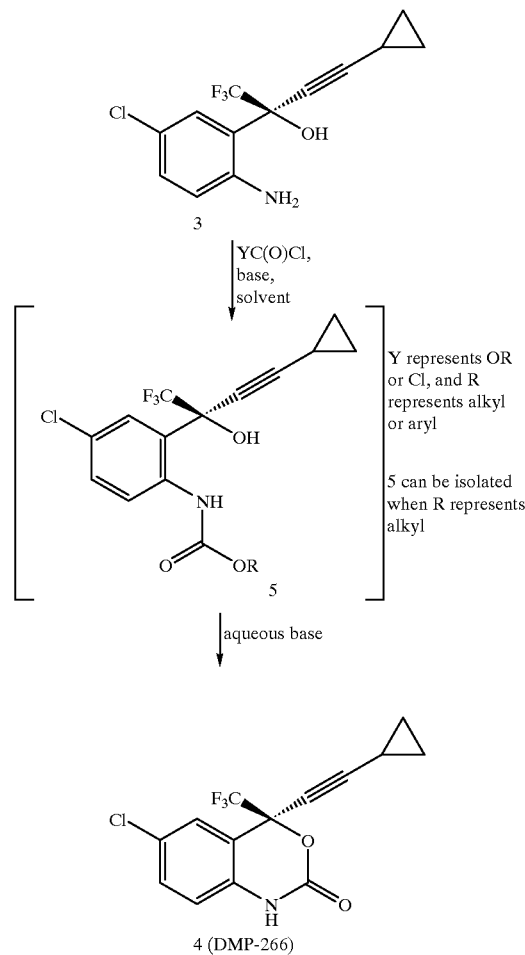

The following examples are meant to be illustrative of the present invention. These examples are presented to exemplify the invention and are not to be construed as limiting the scope of the invention.

EXAMPLE 1

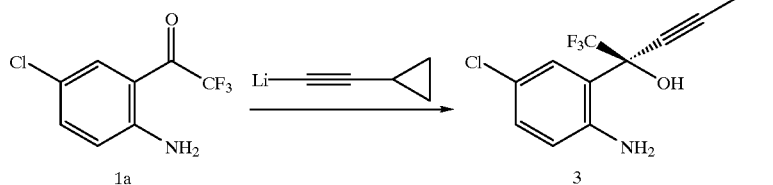

|  | FW | g | mL | mmol | equiv |
|---|---|---|---|---|---|
| Ketone 1a | 323.58 | 4.48 |  | 20 | 1 |
| (1R,2S)-N-pyrrolidinyl norephedrine | 205.30 | 9.85 |  | 48 | 2.4 |
| cyclopropylacetylene | 66.10 | 2.64 |  | 40 | 2 |
| n-BuLi (2.5M in hexane) | 64.06 |  | 16 | 40 | 2 |
| MeOH (4.94M in toluene) |  |  | 9.72 | 48 | 2.4 |
| ZnMe$_2$ (2.0M in toluene) | 32.01 |  | 24 | 48 | 2.4 |
| toluene |  |  | 80 |  |  |
| 1M citric acid |  |  | 45 |  |  |

Into dry toluene (40 mL) is charged (1R,2S)-N-pyrrolidinyl norephedrine (9.85 g, 48 mmol.) and dimethylzinc (2.0M in toluene) under nitrogen. The mixture is stirred for 1 h. Methanol (9.72 mL, 48 mmol.) is added. After 0.5 h the mixture is transferred to a pre-prepared slurry of n-butyllithium (2.5M,16 mL) and cyclopropyl-acetylene (2.64 g., 40 mmol.) in toluene (40 mL) via cannula. A solution of ketone 1a (4.48 g 20 mmol.) is added after 0.5 h. The mixture is stirred for 7 h. Aqueous work up and crystallization gives 4.8 g white solid (83% isolated yield and 83% enantiomeric excess).

EXAMPLE 2

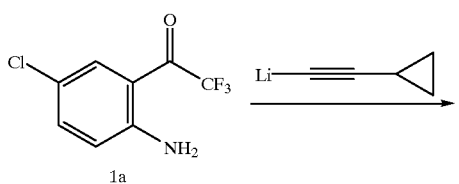
1a

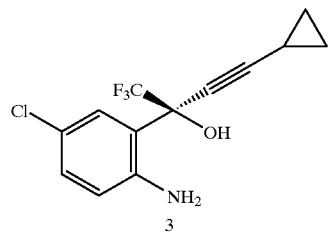
3

Following the procedure outlined in Example 1 above using the first chiral additive noted below in place of (1R,2S)-N-pyrrolidinyl norephedrine, the following assay yields and enantiomeric excesses were obtained:

| first chiral additive | assay yield | enantiomeric excess |
|---|---|---|
| N-methyl ephedrine | 90 | 83 |
| ephedrine | 94 | 28.2 |
| N,N-dibenzyl norephedrine | 95 | 10.4 |
| norephedrine | 25.5 | 41.6 |
| diethyl tartrate | 26.2 | −4 |
| pyrrolidinemethanol | 30 | 16.8 |
| (1R,2R)-pseudoephedrine | 63.3 | 29.8 |
| cinchonine | 90 | −11.2 |
| (1S,2S)-N-methylpseudoephedrine | 28.6 | −43 |

EXAMPLE 3

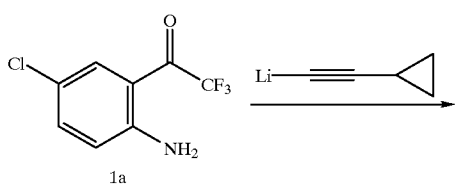
1a

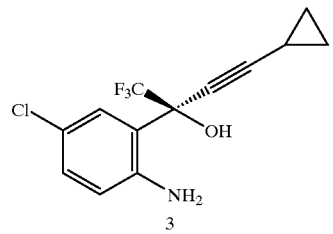
3

Following the procedure outlined in Example 1 above using as the first chiral additive, (1R,2S)-N-pyrrolidinyl norephedrine, with the second additives noted below in place of methanol, the following % enantiomeric excesses were obtained:

| second additive | enantiomeric excess |
|---|---|
| EtOH | 55 |
| i-PrOH | 69 |
| CF₃CO₂H | 76.2 |

EXAMPLE 4

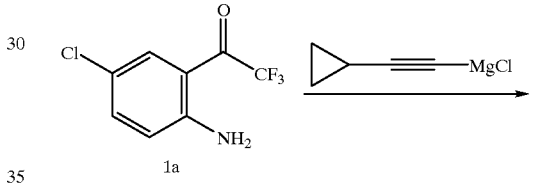
1a

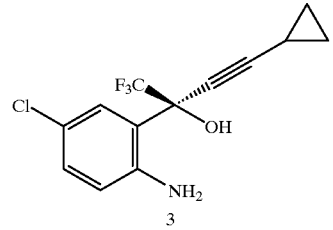
3

Following the procedure outlined in Example 1 above using the first chiral additive, (1R,2S)-N-pyrrolidinyl norephedrine, n-butyl magnesium chloride instead of n-butyl lithium, and the second additive noted below with the reaction run at room temperature, the chiral amino alcohol was produced in the % enantiomeric excess as follows:

| second additive | enantiomeric excess |
|---|---|
| MeOH | 87 |
| t-BuOH | 89.8 |
| (CH₃)₃CCH₂OH | 95.6 |
| (CH₃)₃CCH₂OH | 94* |
| (CH₃)₃CCH(CH₃)OH | 89 |
| Ph₃COH | 74.4 |
| Cl₃CCH₂OH | 96 |
| F₃CCH₂OH | 95.7 |
| CH₂=CHCH₂OH | 90 |
| PhCH₂OH | 89 |
| (CH₃)₂NCH₂CH₂OH | 78.2 |
| 4-NO₂-phenol | 89 |

-continued

| second additive | enantiomeric excess |
|---|---|
| CH$_3$CO$_2$H | 82 |
| CF$_3$CO$_2$H | 89.4 |
| (CH$_3$)CCO$_2$H | 71.6 |

*The reaction temperature was 40° C.

EXAMPLE 5

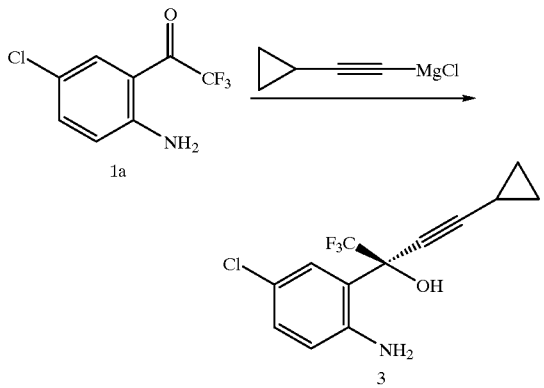

Following the procedure outlined in Example 4 above using (1S,2S)-N-methyl ephedrine as the first chiral additive in place of (1R,2S)-N-pyrrolidinyl norephedrine, and the second additive is (CH$_3$)$_3$CCH$_2$OH, the chiral amino alcohol was produced in an enantiomeric excess of 65.8%.

EXAMPLE 6

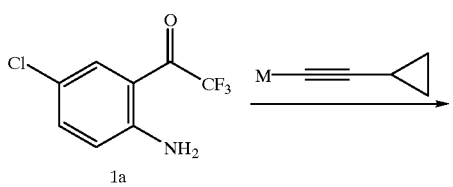

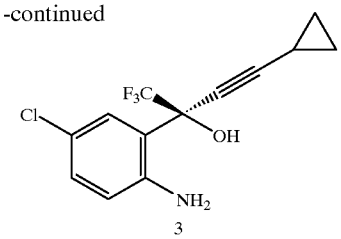

Following the procedure outlined in Example 4 above using the metal noted below in place of lithium, the following assay yields and enantiomeric excesses were obtained:

| M | assay yield | enantiomeric excess |
|---|---|---|
| MgCl | 96 | 87 |
| MgBr | 95 | 53.6 |
| MgI | 76.6 | 50.6 |

EXAMPLE 7

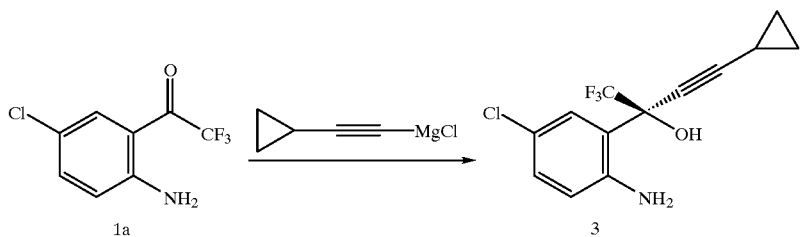

| Materials | Amount | mMol | MW |
|---|---|---|---|
| Ketone 1a | 18.63 g | 83 | 323.58 |
| (1R,2S)-N-pyrrolidinyl norephedrine | 24.64 g | 120 | 205.30 |
| Cyclopropyl acetylene 2 | 6.70 g | 100 | 66.10 |
| n-BuMgCl (2.0 M in THF) | 50 mL | 100 | |
| Neopentyl alcohol (99%) | 7.12 g | 80 | 88.15 |
| ZnMe$_2$ (2.0 M in toluene) | 50 mL | 100 | |
| THF | 100 mL | | |
| 1M Citric Acid | 200 mL | | |

Into an oven dried flask was charged sieves-dried THF (100 mL) and (1R, 2S)-N-pyrrolidinyl norephedrine (24.64 g, 120 mmol) under nitrogen. The mixture was cooled to −20° C. and dimethylzinc (2.0 M in toluene, 50 mL, 100 mmol) was added slowly enough to keep the temperature below 0° C. Neopentyl alcohol (7.12 g, 80 mmol) was then added after 30 min at ambient temperature. The mixture was heated at 60° C. for 1 h and cooled to room temperature. In another dry flask a solution of chloromagnesium cyclopropyl acetylide was prepared by reaction of cyclopropyl acetylene (6.70 g, 100 mmol) and n-butylmagnesium chloride (2.0 M in THF, 50 mL, 100 mmol). The solution was then transferred to the zinc reagent via cannula. After 20 min ketoaniline 1a (18.63 g, 8.33 mmol) was added. The reaction mixture was diluted with hexane (100 mL) and quenched with 1 N citric acid (200 mL) after 7 h. The two layers were separated. The aqueous layer was saved for norephedrine recovery. The organic layer was concentrated to ~50 mL and toluene (100 mL) was added. The solution was concentrated again to ~50 mL to remove all THF. Heptane (80 mL) was slowly added. The solid was collected by filtration and washed with heptane (30 mL) to give 22.62 g (94% yield, 96% ee) of 3 as a white solid.

EXAMPLE 8

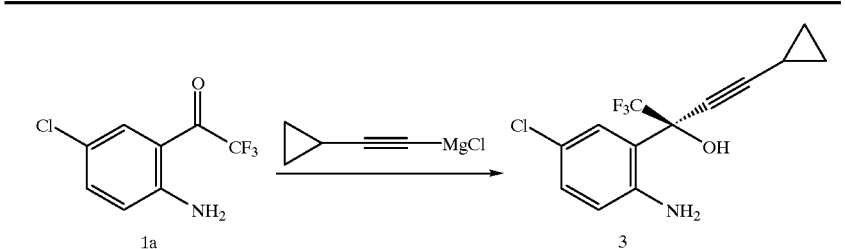

| Materials | Amount | mMol | MW |
| --- | --- | --- | --- |
| Ketone 1a | 9.32 g | 41.7 | 323.58 |
| (1R,2S)-N-pyrrolidinyl norephedrine | 12.32 g | 60 | 205.30 |
| Cyclopropyl acetylene | 3.31 g | 50 | 66.10 |
| n-BuMgCl (2.0 M in THF) | 25 mL | 50 | |
| neopentyl alcohol (99%) | 3.56 g | 40 | 88.15 |
| ZnMe$_2$ (2.0 M in toluene) | 25 mL | 50 | |
| THF | 50 mL | | |
| 1M Citric Acid | 100 mL | | |

Into an oven dried flask was charged sieves-dried THF (50 mL) and (1R, 2S)-N-pyrrolidinyl norephedrine (12.32 g, 60 mmol) under nitrogen. The mixture was cooled to −20° C. and dimethylzinc (2.0 M in toluene, 25 mL, 50 mmol) was added slowly enough to keep the temperature below 0° C. Neopentyl alcohol (3.56 g, 40 mmol) was then added after 30 min at ambient temperature. The mixture was heated at 60° C. for 1 h and cooled to room temperature. In another dry flask a solution of chloromagnesium cyclopropyl acetylide was prepared by reaction of cyclopropyl acetylene (3.31 g, 50 mmol) and n-butylmagnesium chloride (2.0 M in THF, 25 mL, 50 mmol). The solution was then transferred to the zinc reagent via cannula. After 20 min the solution was cooled to 0° C. and ketoaniline 1a (9.32 g, 41.7 mmol) was added. The reaction mixture was diluted with hexane (50 mL) and quenched with 1 N citric acid (100 mL) after 48 h. The two layers were separated. The aqueous layer was saved for norephedrine recovery. The organic layer was concentrated to ~25 mL and toluene (50 mL) was added. The solution was concentrated again to ~25 mL to remove all THF. Heptane (35 mL) was slowly added. The solid was collected by filtration and washed with heptane (10 mL) to give 11.3 g (94% yield, >99% ee) of 3 as a white solid.

$^1$H NMR (CDCl$_3$, 300 MHz): δ 7.52 (1 H), 7.12 (1 H), 6.61 (1 H), 4.70 (1 H), 4.39 (2 H), 1.39 (1 H), and 0.85 (4 H). $^{13}$C NMR (CDCl$_3$, 75.5 MHz) δ 143.21, 130.44, 130.04, 123.94, 123.93 (q), 121.11, 120.81, 93.51, 74.80 (q), 70.58, 88.59, and −0.85.

EXAMPLE 9

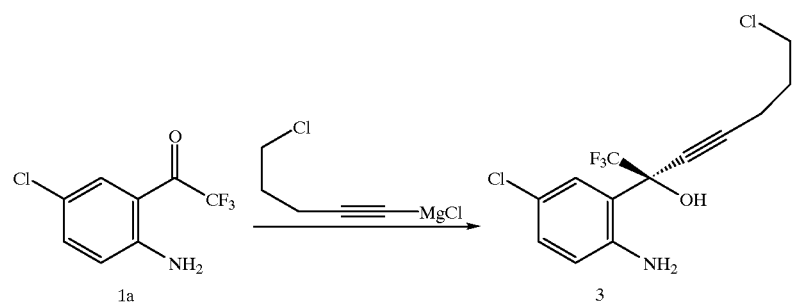

| Materials | Amount | mMol | MW |
| --- | --- | --- | --- |
| Ketone 1a | .93 g | 4.2 | 323.58 |
| (1R,2S)-N-pyrrolidinyl norephedrine | 1.2 g | 6.0 | 205.30 |
| 5-chloropentyne | 3.31 g | 5.0 | 66.10 |

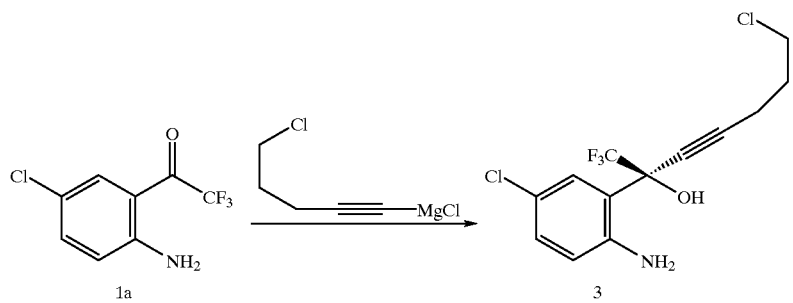

| Materials | Amount | mMol | MW |
|---|---|---|---|
| n-BuMgCl (2.0 M in THF) | 2.5 mL | 5.0 | |
| neopentyl alcohol (99%) | .35 g | 4.0 | 88.15 |
| ZnMe₂ (2.0 M in toluene) | 2.5 mL | 5.0 | |
| THF | 5 mL | | |
| 1M Citric Acid | 20 mL | | |

Into an oven dried flask was charged sieves-dried THF and (1R, 2S)-N-pyrrolidinyl norephedrine under nitrogen. The mixture was cooled to −20° C. and dimethylzinc was added slowly enough to keep the temperature below 0° C. Neopentyl alcohol was then added after 30 min at ambient temperature. The mixture was heated at 60° C. for 1 h and cooled to room temperature. In another dry flask a solution of chloromagnesium 5-chloropentynide was prepared by reaction of 5-chloropentyne and n-butylmagnesium chloride. The solution was then transfered to the zinc reagent via cannula. After 20 min ketoaniline 1a was added. The reaction mixture was diluted with hexane (10 mL) and quenched with 1 N citric acid (20 mL) after 7 h. The two layers were separated. The organic layer was concentrated to ~3 mL and toluene (10 mL) was added. The solution was concentrated again to ~3 mL to remove all THF. Heptane (6 mL) was slowly added. The solid was collected by filtration and washed with heptane (2 mL) to give 1.27 g (93% yield, 95% ee) of 3 as a white solid.

$^1$H NMR (CDCl₃, 300 MHz): δ 7.52 (1 H), 7.12 (1 H), 6.62 (1 H), 4.69 (br, 3 H), 3.69 (2 H), 2.57 (2 H), and 2.06 (2 H). $^{13}$C NMR (CDCl₃, 75.5 MHz) δ 143.18, 130.37, 130.28, 124.18, 122.16, 121.10, 88.49, 77.78, 74.74, 43.42, 30.62, and 16.18.

EXAMPLE 10

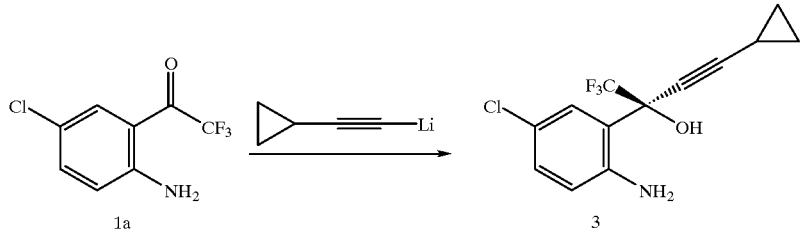

| Materials | Amount | mMol | MW |
|---|---|---|---|
| Ketone 1a | 1.68 g | 7.0 | 323.58 |
| (1R,2S)-N-pyrrolidinyl norephedrine | 0.18 g | .88 | 205.30 |
| cyclopropyl acetylene | 0.66 g | 10 | 66.10 |
| n-BuLi (2.5M in hexane) | 4.0 mL | 10 | |
| methanol | 0.81 mL | 20 | 32.01 |
| ZnMe₂ (2.0M in toluene) | 5 mL | 10 | |
| Toluene | 5 mL | | |
| 1M Citric Acid | 10 mL | | |

Into dry toluene is charged methanol and toluene. The mixture was cooled to −78° C. and dimethylzinc was added under nitrogen. The mixture was allowed to warm to room temperature is and stirred for 1 h. (1R, 2S)-N-pyrrolidinyl norephedrine was added. After 0.5 h the mixture was mixed with a pre-prepared slurry of n-Butyllithium and cyclopropylacetylene in toluene (40 mL) via cannula. Ketone 1 was added after 0.5 h. The mixture is stirred for 7 h. and quenched with excess 1 M citric acid. Assay of the organic solution indicated 83% yield and 20% ee.

EXAMPLE 11

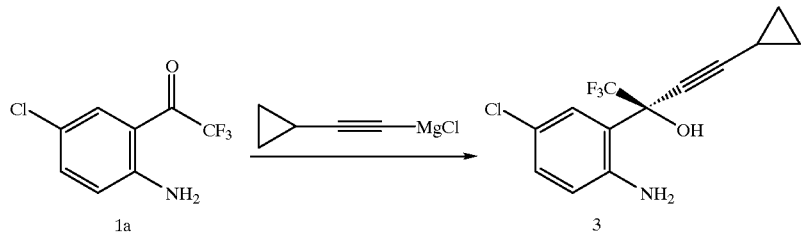

| Materials | Amount | mMol | MW |
|---|---|---|---|
| Ketone 1a | 1.00 kg g | 4.47 | 223.58 |
| (1R,2S)-N-pyrrolidinyl norephedrine | 1.35 kg | 6.58 | 205.30 |
| cyclopropyl acetylene | 361.9 g | 5.47 | 66.10 |
| n-BuMgCl (2.0 M in THF) | 2.68 L | 5.37 | |
| 2,2,2-trifluoroethanol (99%) | 429.5 g | 4.29 | 100.04 |
| ZnEt$_2$ (0.892 M in hexane) | 6.02 L | 5.37 | |
| THF | 9.36 L | | |
| 30% K$_2$CO$_3$ | 550 mL | | |
| 30% citric acid | 2.0 L | | |
| Toluene (for crystallization, 2 mL/g of 4) | 2.6 L | | |
| Heptane (for crystallization, 4 mL/g of 4) | 5.2 L | | |

To a solution of trifluoroethanol and (1R, 2S)-N-pyrrolidinyl norephedrine in THF (9 L) under nitrogen is added a solution of diethylzinc in hexane at 0° C. slowly enough to keep the temperature below 30° C. The mixture is stirred at room temperature for 0.5~1 h. In another dry flask a solution of chloromagnesium cyclopropyl acetylide is prepared as follows: To neat cyclopropyl acetylene at 0° C. is added a solution of n-butylmagnesium chloride slowly enough to keep the internal temperature ≦30° C. The solution is stirred at 0° C. for ~40 min and transfered to the zinc reagent via cannula with 0.36 L of THF as a wash. The mixture is cooled to −10° C. and ketoaniline 1a is added. The mixture is stirred at −2 to −8° C. for 35 h, warmed to room temperature, stirred for 3 h, and quenched with 30% potassium carbonate over 1.5 h. The mixture is stirred for 4 h and the solid is removed by filtration and washed with THF (2 cake volume). The wet solid still contains ~18 wt % of pyrrolidinyl norephedrine and is saved for further study. The filtrate and wash are combined and treated with 30% citric acid. The two layers are separated. The organic layer is washed with water (1.5 L). The combined aqueous layers are extracted with 2.5 L of toluene and saved for norephedrine recovery. The toluene extract is combined with the organic solution and is concentrated to ~2.5 L. Toluene is continuously feeded and distilled till THF is not detectable by GC. The final volume is controlled at 3.9 L. Heptane (5.2 L) is added over 1 h. The slurry is cooled to 0° C., aged for 1 h, and filtered. The solid is washed with heptane (2 cake volume) and dried to give 1.234 Kg (95.2% yield) of amino alcohol 3 as a white crystalline. The material is 99.8 A% pure and 99.3% ee.

EXAMPLE 12

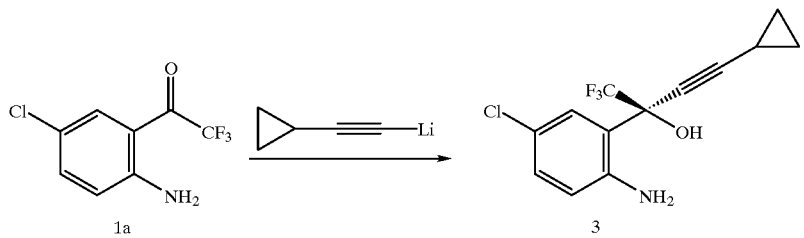

| Materials | Amount | mMol | MW |
|---|---|---|---|
| Ketone 1a | 10.0 g | 44.7 | 223.58 |
| (1R,2S)-N-pyrrolidinyl norephedrine | 13.5 g | 65.7 | 205.30 |
| cyclopropyl acetylene 2 | 36.2 g | 54.8 | 66.10 |
| n-BuLi (2.5 M in hexane) | 21.5 mL | 53.8 | 64.06 |
| 2,2,2-trifluoroethanol (99%) | 4.3 g | 43.0 | 100.04 |
| ZnMe$_2$ (1.0 M in hexane) | 53.7 L | 53.7 | |
| THF | 150 mL | | |

Into a solution of trifluoroethanol, (1R, 2S)-N-pyrrolidinyl norephedrine in THF (60 mL) under nitrogen is added a solution of diethylzinc in hexane at 0° C. slowly enough to keep the temperature below 30° C. The mixture is stirred at room temperature for 0.5~1 h. In another dry flask a solution of lithium cyclopropyl acetylide is prepared as follows: To a solution of cyclopropyl acetylene in THF (80 mL) at 0° C. is added a solution of n-butyllithium slowly enough to keep the internal temperature ≦30° C. The mixture is stirred at 0° C. for ~40 min. The zinc reagent is then transferred into the cloudy lithium acetylide solution via cannula with 10 mL of THF as a wash. The mixture is aged for 0.5 h and ketoaniline 1 is added. The mixture is stirred at room temperature for 15.5 h. HPLC assay of this solution indicated about 74% yield and 89% ee.

chloroformate was added, in 4 batches, at 25° C. During the addition the solution pH was monitored. The pH was maintained between 8.5 and 4 during the reaction and ended up at 8.0. The mixture was stirred at 20–25° C. for two hours. Aqueous KOH (2N) was added over 20 minutes, until the pH of the aqueous layer reached 11.0.

The layers were separated and 500 mL brine was added to the MTBE layer. 0.1 N Acetic acid was added until the pH was 6–7. The layers were separated and the organic phase was washed with brine (500 mL). At this point the mixture

EXAMPLE 13

|  | FW | g | mL | mmol | equiv |
|---|---|---|---|---|---|
| amino alcohol 3 | 289 | 100 |  | 346 | 1 |
| 4-nitrophenylchloroformate | 201.6 | 73.2 |  | 363 | 1.05 |
| KHCO$_3$ | 100 | 45 |  | 450 | 1.3 |
| 2N KOH | 56 |  | 346 | 692 | 2.0 |
| H$_2$O |  |  | 654 |  |  |
| MTBE |  |  | 500 |  |  |

To a three necked round bottom flask, equipped with a mechanical stirrer, nitrogen line, and thermocouple, was charged the solid amino alcohol 3, MTBE (500 mL), and aqueous KHCO$_3$ (45 g in 654 mL H$_2$O). Solid 4-nitrophenyl was solvent switched to EtOH/IPA and crystallized as recited in Examples 16 and 17.

EXAMPLE 14

|  | FW | g | mL | mmol | equiv |
|---|---|---|---|---|---|
| amino alcohol 3a | 289 | 100 |  | 346 | 1 |
| phosgene (20 wt % in toluene) | 99 | 41 | 216 | 415 | 1.2 |
| KHCO$_3$ | 100 | 86.5 |  | 865 | 2.5 |
| H$_2$O |  |  | 500 |  |  |
| Toluene |  |  | 500 |  |  |

To a three necked round bottom flask, equipped with a mechanical stirrer, nitrogen line, and thermocouple, was charged the solid amino alcohol 3a, toulene (500 mL), and aqueous $KHCO_3$ (86.5 g in 500 mL $H_2O$). Phosgene solution in toulene was added at 25° C., and the mixture was stirred at 20–25° C. for two hours.

The layers were separated and the organic phase was washed with brine (500 mL). At this point the mixture was solvent switched to EtOH/IPA and crystallized as recited in Examples 16 and 17.

EXAMPLE 15

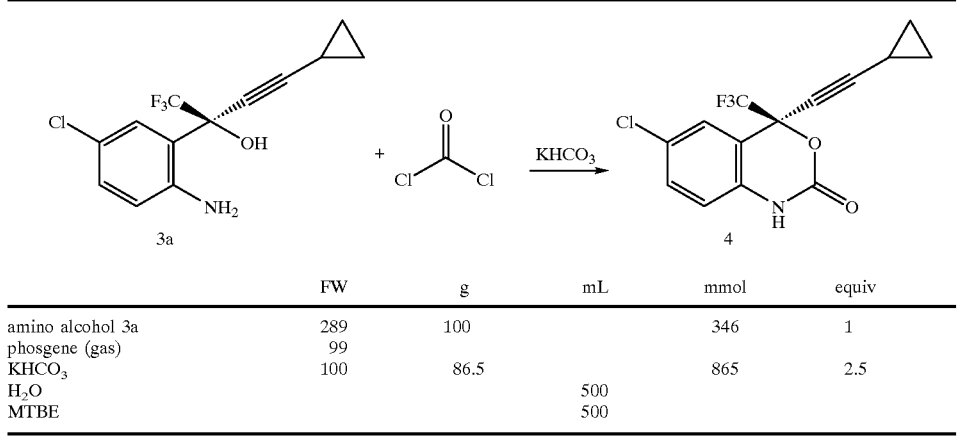

| | FW | g | mL | mmol | equiv |
|---|---|---|---|---|---|
| amino alcohol 3a | 289 | 100 | | 346 | 1 |
| phosgene (gas) | 99 | | | | |
| $KHCO_3$ | 100 | 86.5 | | 865 | 2.5 |
| $H_2O$ | | | 500 | | |
| MTBE | | | 500 | | |

To a three necked round bottom flask, equipped with a mechanical stirrer, nitrogen line, and thermocouple, was charged the solid amino alcohol 3a, MTBE (500 mL), and aqueous $KHCO_3$ (86.5 g in 500 mL $H_2O$). Phosgene gas was slowly passed into the solution at 25° C., until the reaction was complete.

The layers were separated and the organic phase was washed with brine (500 mL). At this point the mixture was solvent switched to EtOH/IPA and crystallized as recited in Examples 16 and 17.

EXAMPLE 16

Crystallization of DMP-266 from 30% 2-Propanol in Water using a ratio of 15 ml solvent per gram DMP-266 Using Controlled Anti-Solvent Addition on a 400 g Scale.

400 g. of DMP-266 starting material is dissolved in 1.8 L of 2-propanol. The solution is filtered to remove extraneous matter. 1.95 L of deionized (DI) water is added to the solution over 30 to 60 minutes. 10 g. to 20 g. of DMP-266 seed (Form II wetcake) is added to the solution. The seed bed is aged for 1 hour. The use of Intermig agitators is preferred to mix the slurry. If required (by the presence of extremely long crystals or a thick slurry), the slurry is wet-milled for 15–60 seconds. 2.25 L of DI water is added to the slurry over 4 to 6 hours. If required (by the presence of extremely long crystals or a thick slurry), the slurry is wet-milled for 15–60 seconds during the addition. The slurry is aged for 2 to 16 hours until the product concentration in the supernatant remains constant. The slurry is filtered to isolate a crystalline wet cake. The wet cake is washed with 1 to 2 bed volumes of 30% 2-propanol in water and then twice with 1 bed volume of DI water each. The washed wet cake is dried under vacuum at 50° C.

EXAMPLE 17

Crystallization of DMP-266 from 30% 2-Propanol in Water using a ratio of 15 ml solvent per gram DMP-266 Using a Semi-Continuous Process on a 400 g Scale.

400 g. of DMP-266 starting material is dissolved in 1.8 L of 2-propanol. A heel slurry is produced by mixing 20 g. of Form II DMP-266 in 0.3 L of 30% (v/v) 2-propanol in water or retaining part of a slurry from a previous crystallization in the crystallizer. The dissolved batch and 4.2 L of DI water are simultaneously charged to the heel slurry at constant rates over 6 hours to maintain a constant solvent composition in the crystallizer. Use of Intermig agitators during the crystallization is preferred. During this addition the slurry is wet-milled when the crystal lengths become excessively long or the slurry becomes too thick. The slurry is aged for 2 to 16 hours until the product concentration in the supernatant remains constant. The slurry is filtered to isolate a crystalline wet cake. The wet cake is washed with 1 to 2 bed volumes of 30% 2-propanol in water and then twice with 1 bed volume of DI water each. The washed wet cake is dried under vacuum at 50° C.

EXAMPLE 18
Preparation of Amino Alcohol 3 and ee Upgrading—Through Process

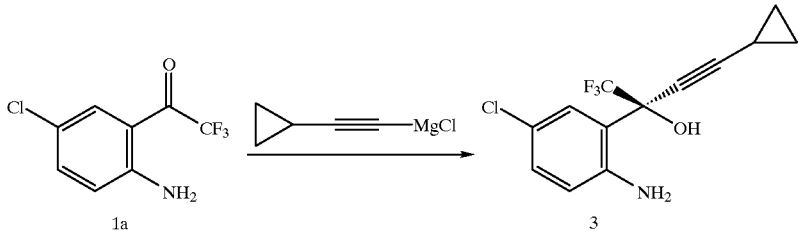

| Materials | Amount | Mol | MW |
|---|---|---|---|
| Ketone 1 | 1.00 kg | 4.47 | 223.58 |
| (1R,2S)-N-Pyrrolidinyl norephedrine | 1.35 kg | 6.58 | 205.30 |
| Cyclopropyl acetylene | 361.9 g | 5.47 | 66.10 |
| n-BuMgCl (2.0 M in THF) | 2.68 L | 5.37 | |
| Trifluoroethanol (99%) | 429.5 g | 4.29 | 100.04 |
| ZnEt$_2$ (0.892 M in hexane) | 6.02 L | 5.37 | |
| THF | 9.36 L | | |
| 30% K$_2$CO$_3$ | 1.2 L | | |
| 1 M Citric acid | 3.5 L | | |
| Heptane | 12 L | | |
| Isopropyl acetate (IPAc) | 40 L | | |
| 12N HCl | 405 mL | 4.88 | |
| tert-Butylmethyl ether (MTBE) | 6 L | | |
| Toluene | 6.25 L | | |
| Na$_2$CO$_3$ | 1.2 kg | 11.25 | |

A solution of diethyl zinc in hexane was added to a solution of trifluoroethanol (429.5 g, 4.29 mol) and (1R, 2S)-N-pyrrolidinyl norephedrine (1.35 kg, 6.58 mol) in THF (9 L), under nitrogen, at 0° C. The resulting mixture was stirred at room temperature for approx. 30 min. In another dry flask a solution of chloromagnesium-cyclopropylacetylide was prepared as follows. To a solution of n-butylmagnesium chloride in THF (2 M, 2.68 L, 5.37 mol) was added neat cyclopropylacetylene at 0° C. keeping the temperature ≦25° C. The solution was stirred at 0° C. for 1~2 h. The solution of chloromagnesiumcyclopropylacetylide was then warmed to room temperature and was transferred into the zinc reagent via cannula over 5 min followed by vessel rinse with 0.36 L of THF. The resulting mixture was aged at ~30° C. for 0.5 h and was then cooled to 20° C. The ketoaniline 1 (1.00 kg, 4.47 mol) was added in one portion as a solid, and the resulting mixture was stirred at 20–28° C. for 3 h.

The reaction was quenched with 30% aq. potassium carbonate (1.2 L) and aged for 1 h. The solid waste was filtered and the cake was washed with THF (3 cake volumes). The filtrate and wash were combined and solvent switched to IPAc.

The IPAc solution of product 3 and pyrrolidinyl norephedrine was washed with citric acid (3.5 L) and with water (1.5 L). The combined aqueous layers were extracted with IPAc (2 L) and saved for norephedrine recovery. To the combined organic layers was added 12N HCl (405 mL, 4.88 mol), to form a thin slurry of the amino alcohol-HCl salt. The mixture was aged for 30 min at 25° C. and was then dried azeotropically.

The slurry was aged at 25° C. for 30 min and filtered. The cake was washed with 2.5 L of IPAc and dried at 25° C. under vacuum/nitrogen for 24 h to give 1.76 kg of the wet HCl salt.

The salt was dissolved in a mixture of MTBE (6 L) and aq Na$_2$CO$_3$ (1.18 kg in 6.25 L water). The layers were separated and the organic layer was washed with 1.25 L of water. The organic layer was then solvent switched into toluene.

Heptane (5 L) was added over 1 h at 25° C. The slurry was cooled to 0° C., aged for 1 h, and filtered. The solid was washed with heptane (2 cake volumes) and was dried to give 1.166 kg (90% overall yield) of amino alcohol 3 as a white crystalline solid.

Norephedrine recovery

The aqueous solution was basified to pH13 using 50% aq NaOH, and extracted with heptane (2 L). The heptane solution was washed with water (1 L) and concentrated to remove residual IPAc and water. The final volume was adjusted to about 3 L. The heptane solution was cooled to −20° C., aged for 2 h, and filtered. The solid was washed with cold heptane (1 cake volume) and dried to give 1.269 kg solid (94% recovery).

What is claimed is:

1. A process for the preparation of a compound of formula I:

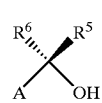

or its enantiomer, wherein

A is:
(a) $C_1$–$C_6$-alkyl, $C_2$–$C_6$-alkenyl, or $C_2$–$C_6$-alkynyl, unsubstituted or mono- or di-substituted with a substituent selected from the group consisting of: halo, $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, $NHCONH(C_1$–$C_6$-alkyl), $NHCON(C_1$–$C_6$-alkyl)$_2$, $CO_2$—$C_1$–$C_6$-alkyl, $C_3$–$C_7$-cycloalkyl, or $C_1$–$C_6$-alkoxy;
(b) phenyl, biphenyl, or naphthyl, unsubstituted or substituted with one to four substituents selected from $R^1$, $R^2$, $R^3$, and $R^4$;

37

$R^1$, $R^2$, $R^3$, and $R^4$ are independently:
    halo, $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, $CON(C_1-C_6\text{-alkyl})_2$, $NHCONH_2$, NHCONH$(C_1-C_6\text{-alkyl})$, $NHCON(C_1-C_6\text{-alkyl})_2$, aryl, $CO_2$—$C_1-C_6\text{-alkyl}$, $C_1-C_6\text{-alkyl}$, $C_2-C_6\text{-alkenyl}$, $C_2-C_6\text{-alkynyl}$, $C_3-C_7\text{-cycloalkyl}$, or $C_1-C_6\text{-alkoxy}$, such that $C_1-C_6$-alkyl is unsubstituted or substituted with aryl, aryl is defined as phenyl, biphenyl, or naphthyl, unsubstituted or substituted with $C_1-C_6$-alkyl, $C_1-C_6$-alkoxy, $NO_2$, or halo;

$R^5$ is:
    (a) H,
    (b) $C_1-C_6\text{-alkyl}$, $C_2-C_6\text{-alkenyl}$, or $C_2-C_6\text{-alkynyl}$, unsubstituted or mono- or di-substituted with a substituent selected from the group consisting of: halo, $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, $CON(C_1-C_6\text{-alkyl})_2$, $NHCONH_2$, $NHCONH(C_1-C_6\text{-alkyl})$, $NHCON(C_1-C_6\text{-alkyl})_2$, $CO_2$—$C_1-C_6\text{-alkyl}$, $C_3-C_7\text{-cycloalkyl}$, or $C_1-C_6\text{-alkoxy}$;
    (c) $C_1-C_4$-perfluoroalkyl, $R^6$ is:
    $C_1-C_6\text{-alkyl}$, $C_2-C_6\text{-alkenyl}$, or $C_2-C_6\text{-alkynyl}$, unsubstituted or mono- or di-substituted with a substituent selected from the group consisting of: halo, $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, $CON(C_1-C_6\text{-alkyl})_2$, $NHCONH_2$, $NHCONH(C_1-C_6\text{-alkyl})$, $NHCON(C_1-C_6\text{-alkyl})_2$, $CO_2$—$C_1-C_6\text{-alkyl}$, $C_3-C_7$-cycloalkyl or $C_1-C_6\text{-alkoxy}$;

comprising the steps of:
    a) adding slowly a dialkylzinc in a solvent or neat, to a first chiral additive bearing one or more exchangeable protons, or alternatively, to a mixture of a first chiral additive bearing one and only one exchangeable proton and a second additive, in a solvent under an inert atmosphere at a temperature of about −78° C. to about 50° C. to form a chiral zinc complex or a second additive containing chiral zinc complex;
    b) adding a second additive to a chiral zinc complex, and heating the reaction to about 10° C. to about 70° C. to form a second additive containing chiral zinc complex, where the first chiral additive bears one and only one exchangeable proton, or alternatively, skipping this addition step where the first chiral additive bears more than one exchangeable proton, or the second additive was added in step a);
    c) mixing the chiral zinc complex or the second additive containing chiral zinc complex with an organometallic reagent of formula, $R^6M$, where M is: Li, Na, K, Zn, $MgX_1$, $CuX_1$, or $B(X_1)_2$; and $X_1$ is Cl, Br, I, F, or $CF_3SO_2$; in a solvent at a temperature range of −20° C. to about 60° C. to form a chiral organozinc complex; and
    d) mixing a carbonyl-containing compound of formula:

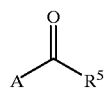

optionally dissolved in a solvent with the solution of the chiral organozinc complex under an inert atmosphere at a temperature of about −20° C. to about 60° C. for about 1 hour to about 72 hours.

38

2. The process as recited in claim 1, for the preparation of a compound of formula I:

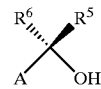

I or its enantiomer, wherein

A is:
    (a) $C_1-C_6\text{-alkyl}$, $C_2-C_6\text{-alkenyl}$, or $C_2-C_6\text{-alkynyl}$, unsubstituted or mono- or di-substituted with a substituent selected from the group consisting of: halo (Cl, Br, F, I), $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, $CON(C_1-C_6\text{-alkyl})_2$, $NHCONH_2$, NHCONH$(C_1-C_6\text{-alkyl})$, $NHCON(C_1-C_6\text{-alkyl})_2$, $CO_2$—$C_1-C_6\text{-alkyl}$, $C_3-C_7\text{-cycloalkyl}$, or $C_1-C_6\text{-alkoxy}$;
    (b) phenyl, biphenyl, or naphthyl, unsubstituted or substituted with one to four substituents selected from $R^1$, $R^2$, $R^3$, and $R^4$;

$R^1$, $R^2$, $R^3$, and $R^4$ are independently:
    halo (Cl, Br, F, I), $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, $CON(C_1-C_6\text{-alkyl})_2$, $NHCONH_2$, NHCONH$(C_1-C_6\text{-alkyl})$, $NHCON(C_1-C_6\text{-alkyl})_2$, aryl, $CO_2$—$C_1-C_6\text{-alkyl}$, $C_1-C_6\text{-alkyl}$, $C_2-C_6\text{-alkenyl}$, $C_2-C_6\text{-alkynyl}$, $C_3-C_7\text{-cycloalkyl}$, or $C_1-C_6\text{-alkoxy}$, such that $C_1-C_6$-alkyl is unsubstituted or substituted with aryl, aryl is defined as phenyl, biphenyl, or naphthyl, unsubstituted or substituted with $C_1-C_6$-alkyl, $C_1-C_6$-alkoxy, $NO_2$, or halo (Cl, Br, F, I);

$R^5$ is:
    (a) H,
    (b) $C_1-C_6\text{-alkyl}$, $C_2-C_6\text{-alkenyl}$, or $C_2-C_6\text{-alkynyl}$, unsubstituted or mono- or di-substituted with a substituent selected from the group consisting of: halo (Cl, Br, F, I), $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, $CON(C_1-C_6\text{-alkyl})_2$, $NHCONH_2$, NHCONH$(C_1-C_6\text{-alkyl})$, $NHCON(C_1-C_6\text{-alkyl})_2$, $CO_2$—$C_1-C_6\text{-alkyl}$, $C_3-C_7\text{-cycloalkyl}$, or $C_1-C_6\text{-alkoxy}$;
    (c) $C_1-C_4$-perfluoroalkyl, $R^6$ is:
    $C_1-C_6\text{-alkyl}$, $C_2-C_6\text{-alkenyl}$, or $C_2-C_6\text{-alkynyl}$, unsubstituted or mono- or di-substituted with a substituent selected from the group consisting of: halo (Cl, Br, F, I), $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, $CON(C_1-C_6\text{-alkyl})_2$, $NHCONH_2$, NHCONH$(C_1-C_6\text{-alkyl})$, $NHCON(C_1-C_6\text{-alkyl})_2$, $CO_2$—$C_1-C_6\text{-alkyl}$, $C_3-C_7$-cycloalkyl or $C_1-C_6\text{-alkoxy}$;

comprising the steps of:
    a) adding slowly a dialkylzinc in a solvent or neat, to a first chiral additive in a solvent under an inert atmosphere at a temperature of about −78° C. to about 50° C. to form a chiral zinc complex;
    b) adding a second additive to the chiral zinc complex, and heating the reaction to about 10° C. to about 70° C. to form a second additive containing chiral zinc complex, where the first chiral additive bears one and only one exchangeable proton;
    c) mixing the second additive containing chiral zinc complex with an organometallic reagent of formula, $R^6M$, where M is: Li, Na, K, Zn, $MgX_1$, $CuX_1$, or $B(X_1)_2$; and $X_1$ is Cl, Br, I, F, or $CF_3SO_2$; in a solvent at a temperature range of $-20°$ C. to about $60°$ C. to form a chiral organozinc complex; and d) mixing a carbonyl-containing compound of formula:

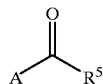

optionally dissolved in a solvent with the solution of the chiral organozinc complex under an inert atmosphere at a temperature of about $-20°$ C. to about $60°$ C. for about 1 hour to about 72 hours.

3. The process as recited in claim 1, for the preparation of a compound of formula I:

I or its enantiomer, wherein

A is:
(a) $C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, $NHCONH(C_1$–$C_6$-alkyl), $NHCON(C_1$–$C_6$-alkyl)$_2$, $CO_2$—$C_1$–$C_6$-alkyl, $C_3$–$C_7$-cycloalkyl, or $C_1$–$C_6$-alkoxy;

(b) phenyl, biphenyl, or naphthyl, unsubstituted or substituted with one to four substituents selected from $R^1$, $R^2$, $R^3$, and $R^4$;

$R^1$, $R^2$, $R^3$, and $R^4$ are independently:
halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, $NHCONH(C_1$–$C_6$-alkyl), $NHCON(C_1$–$C_6$-alkyl)$_2$, aryl, $CO_2$—$C_1$–$C_6$-alkyl, $C_1$–$C_6$-alkyl, $C_2$–$C_6$-alkenyl, $C_2$–$C_6$-alkynyl, $C_3$–$C_7$-cycloalkyl, or $C_1$–$C_6$-alkoxy, such that $C_1$–$C_6$-alkyl is unsubstituted or substituted with aryl, aryl is defined as phenyl, biphenyl, or naphthyl, unsubstituted or substituted with $C_1$–$C_6$-alkyl, $C_1$–$C_6$-alkoxy, $NO_2$, or halo;

$R^5$ is:
(a) H,
(b) $C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, $NHCONH(C_1$–$C_6$-alkyl), $NHCON(C_1$–$C_6$-alkyl)$_2$, $CO_2$—$C_1$–$C_6$-alkyl, $C_3$–$C_7$-cycloalkyl, or $C_1$–$C_6$-alkoxy;
(c) $C_1$–$C_4$-perfluoroalkyl, $R^6$ is:
$C_1$–$C_6$-alkyl, $C_2$–$C_6$-alkenyl, or $C_2$–$C_6$-alkynyl, unsubstituted or mono- or di-substituted with a substituent selected from the group consisting of: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, $NHCONH(C_1$–$C_6$-alkyl), $NHCON(C_1$–$C_6$-alkyl)$_2$, $CO_2$—$C_1$–$C_6$-alkyl, $C_3$–$C_7$-cycloalkyl or $C_1$–$C_6$-alkoxy;

comprising the steps of:

a) adding slowly a dialkylzinc in a solvent or neat, to a mixture of a first chiral additive bearing one and only one exchangeable proton and a second additive, in a solvent under an inert atmosphere at a temperature of about $-78°$ C. to about $50°$ C. to form a second additive containing chiral zinc complex;

b) mixing the second additive containing chiral zinc complex with an organometallic reagent of formula, $R^6M$, where M is: Li, Na, K, Zn, $MgX_1$, $CuX_1$, or $B(X_1)_2$; and $X_1$ is Cl, Br, I, F, or $CF_3SO_2$; in a solvent at a temperature range of $-20°$ C. to about $60°$ C. to form a chiral organozinc complex; and c) mixing a carbonyl-containing compound of formula:

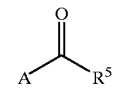

optionally dissolved in a solvent with the solution of the chiral organozinc complex under an inert atmosphere at a temperature of about $-20°$ C. to about $60°$ C. for about 1 hour to about 72 hours.

4. The process as recited claim 1, wherein the first chiral additive has the formula:

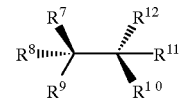

or its enantiomer or diastereomer, and the substituents are defined as:

$R^9$ and $R^{10}$ are independently:
OH, $NH_2$, $NHR^{17}$, $N(R^{17})_2$, or

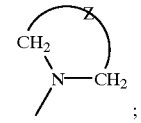

;

$R^7$, $R^8$, $R^{11}$ and $R^{12}$ are independently:
(a) H,
(b) $CF_3$,
(c) CN,
(d) $CONH_2$,
(e) $CONH(C_1$–$C_6$-alkyl),
(f) $CON(C_1$–$C_6$-alkyl)$_2$,
(g) $CO_2$—$C_1$–$C_6$-alkyl,
(h) $C_3$–$C_7$-cycloalkyl,
(i) $C_1$–$C_6$-alkyl, $C_2$–$C_6$-alkenyl, or $C_2$–$C_6$-alkynyl, unsubstituted or mono- or di-substituted with a substituent selected from the group consisting of: halo, $CF_3$, CN, $NO_2$, $NH_2$, $NH(C_1$–$C_6$-alkyl), $N(C_1$–$C_6$-alkyl)$_2$, $CONH_2$, $CONH(C_1$–$C_6$-alkyl), $CON(C_1$–$C_6$-alkyl)$_2$, $NHCONH_2$, $NHCONH(C_1$–$C_6$-alkyl), $NHCON(C_1$–$C_6$-alkyl)$_2$, $CO_2$—$C_1$–$C_6$-alkyl, $C_3$–$C_7$-cycloalkyl, $C_1$–$C_6$-alkoxy;
(j) $R^7$ and $R^8$ or $R^{11}$ and $R^{12}$ taken together can represent =O, forming a ketone, amide, acid or ester group;

(k)

such that one and only one of $R^7$, $R^8$, $R^{11}$, or $R^{12}$ can bear this definition,
except that at least one of the two carbons bearing $R^7$, $R^8$, $R^9$, $R^{10}$, $R^{11}$ and $R^{12}$ is a chiral center;

$R^9$ taken together with either $R^{11}$ or $R^{12}$ can represent:

such that the other of $R^{11}$ or $R^{12}$ is hydrogen; or
$R^{10}$ taken together with either $R^7$ or $R^8$ can represent:

such that the other of $R^7$ or $R^8$ is hydrogen;

$R^{13}$ is: H, $C_1$–$C_6$-alkyl, or phenyl;

$R^{14}$ is: H, except that $R^7$ or $R^8$ and $R^{14}$ taken together can represent a carbon carbon bond, when t is 1 or 2 and $R^{11}$ or $R^{12}$ represents or
$R^7$ or $R^8$ and $R^{14}$ taken together can represent —$(CH_2)_s$—, when t is 0 and $R^{11}$ or $R^{12}$ represents $R^{15}$ or $R^{16}$ is: $C_1$–$C_6$-alkyl, $C_2$–$C_6$-alkenyl, or $C_2$–$C_6$-alkynyl, unsubstituted or mono- or di-substituted with a substituent selected from the group consisting of: halo, $CF_3$, CN, $NO_2$, $NH_2$, NH($C_1$–$C_6$-alkyl), N($C_1$–$C_6$-alkyl)$_2$, $CONH_2$, CONH($C_1$–$C_6$-alkyl), CON($C_1$–$C_6$-alkyl)$_2$, $NHCONH_2$, NHCONH($C_1$–$C_6$-alkyl), NHCON($C_1$–$C_6$-alkyl)$_2$, $CO_2$—$C_1$–$C_6$-alkyl, $C_3$–$C_7$-cycloalkyl, $C_1$–$C_6$-alkoxy; such that the other of $R^{15}$ and $R^{16}$ is hydrogen;

$R^{17}$ is: $C_1$–$C_6$-alkyl, unsubstituted or substituted with aryl, or aryl, wherein aryl is defined as phenyl or naphthyl;

Z represents:

represents a six-membered ring, unsaturated or saturated, optionally substituted with one or two heteroatoms selected from N, O, or S, optionally substituted with $C_1$–$C_6$-alkyl;

represents: a five-membered ring, unsaturated or saturated, optionally substituted with one or two heteroatoms selected from N, O, or S, optionally substituted with $C_1$–$C_6$-alkyl;

n is 1, 2, or 3;

m is 0, or 1;

t is 0, 1, or 2; and s is 1 or 2.

5. The process as recited in claim 4, wherein dialkylzinc is defined as a [$C_1$–$C_6$-alkyl]$_2$Zn.

6. The process as recited in claim 5, wherein the second additive is defined as: ROH, RSH, $RCO_2H$, $RSO_3H$, HX, $RCONH_2$, or aryl$NH_2$; and R is $C_1$–$C_6$-alkyl, $C_2$–$C_6$- alkenyl, $C_2$–$C_6$-alkynyl, aryl, where aryl is defined as phenyl or naphthyl, and heteroaryl, where heteroaryl is defined as a 5 or 6-membered aromatic ring substituted with one or two heteroatoms selected from O, S, N, and each of which is unsubstituted or substituted with one, two or three substituents selected from the group consisting of: $NO_2$, Cl, Br, I, F, $CF_3$, $C_1$–$C_6$-alkyl, $C_1$–$C_6$-alkoxy, and $N[C_1$–$C_6$-alkyl$]_2$; and X is Cl, Br, I, or F.

7. The process as recited in claim 6, wherein the solvent is defined as a polar or non-polar aprotic solvent, or mixtures of said solvents.

8. The process as recited in claim 7, wherein the first chiral additive is selected from the group consisting of: (1R, 2S)-N-pyrrolidinyl norephedrine, N-methylephedrine, ephedrine, N,N-dibenzylnorephedrine, norephedrine, diethyl tartrate, pyrrolidine-methanol, (1R,2R)-pseudoephedrine, cinchonine, and (1S,2S)-N-methylpseudoephedrine.

9. The process as recited in claim 8, wherein the dialkylzinc is diethylzinc and dimethylzinc.

10. The process as recited in claim 9, wherein the second additive is defined as: MeOH, t-BuOH, $(CH_3)_3CCH_2OH$, $(CH_3)_3CCH(CH_3)OH$, $Ph_3COH$, $Cl_3CCH_2OH$, $F_3CCH_2OH$, $CH_2=CHCH_2OH$, $PhCH_2OH$, $(CH_3)_2NCH_2CH_2OH$, 4-$NO_2$-phenol, $CH_3CO_2H$, $CF_3CO_2H$, and $(CH_3)CCO_2H$.

11. The process as recited in claim 10, wherein the the solvent is tetrahydrofuran, benzene, chlorobenzene, o-, m-, p-dichlorobenzene, dichloromethane, toluene, hexane, cyclohexane, pentane, methyl t-butyl ether, diethyl ether, N-methylpyrrolidine, or mixtures of said solvents.

12. A process for the preparation of an amino alcohol of formula:

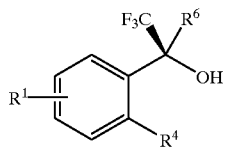

wherein:

$R^1$ is:
halo, $CF_3$, CN, $NO_2$, $NH_2$, NH($C_1$–$C_6$-alkyl), N($C_1$–$C_6$-alkyl)$_2$, $CONH_2$, CONH($C_1$–$C_6$-alkyl), CON($C_1$–$C_6$-alkyl)$_2$, $NHCONH_2$, NHCONH ($C_1$–$C_6$-alkyl), NHCON($C_1$–$C_6$-alkyl)$_2$, aryl, $CO_2$—$C_1$–$C_6$-alkyl, $C_1$–$C_6$-alkyl, $C_2$–$C_6$-alkenyl, $C_2$–$C_6$-alkynyl, $C_3$–$C_7$-cycloalkyl, or $C_1$–$C_6$-alkoxy, such that $C_1$–$C_6$-alkyl is unsubstituted or substituted with aryl, aryl is defined as phenyl, biphenyl, or naphthyl, unsubstituted or substituted with $C_1$–$C_6$-alkyl, $C_1$–$C_6$-alkoxy, $NO_2$, or halo;

$R^4$ is:
$NH_2$, or NH($C_1$–$C_6$-alkyl), such that $C_1$–$C_6$-alkyl is unsubstituted or substituted with aryl, aryl is defined as phenyl or naphthyl, unsubstituted or substituted with $C_1$–$C_6$-alkyl, $C_1$–$C_6$-alkoxy, $NO_2$, or halo;

$R^6$ is:
$C_1$–$C_6$-alkyl, $C_2$–$C_6$-alkenyl, or $C_2$–$C_6$-alkynyl, unsubstituted or mono- or di-substituted with a substituent selected from the group consisting of: halo, $CF_3$, CN, $NO_2$, $NH_2$, NH($C_1$–$C_6$-alkyl), N($C_1$–$C_6$-alkyl)$_2$, $CONH_2$, CONH($C_1$–$C_6$-alkyl), CON($C_1$–$C_6$-alkyl)$_2$, $NHCONH_2$, NHCONH($C_1$–$C_6$-alkyl), NHCON ($C_1$–$C_6$-alkyl)$_2$, $CO_2$—$C_1$–$C_6$-alkyl, $C_3$–$C_7$-cycloalkyl, or $C_1$–$C_6$-alkoxy;

comprising the steps of:

a) adding slowly a dialkylzinc in a solvent or neat, to a first chiral additive bearing one or more exchangeable protons, or, alternatively, to a mixture of a first chiral additive bearing one and only one exchangeable proton, and a second additive, in a solvent under an inert atmosphere at a temperature of about −78° C. to about 50° C. to form a chiral zinc complex or a second additive containing chiral zinc complex;

b) adding a second additive to the chiral zinc complex, and heating the reaction to about 10° C. to about 70° C. to form a second additive containing chiral zinc complex, where the first chiral additive bears one and only one exchangeable proton, or, alternatively, skipping this addition step where the first chiral additive bears more than one exchangeable proton, or the second additive was added in step a);

c) mixing the chiral zinc complex or the second additive containing chiral zinc complex with an organometallic reagent of formula, $R^6M$, wherein M represents: Na, K, Li, $MgX_1$, $ZnX_1$, $CuX_1$, or $B(X_1)_2$; and $X_1$ is Cl, Br, I, F, or $CF_3SO_2$; in a solvent to form a chiral organozinc complex; and d) mixing a ketone of formula:

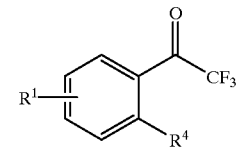

optionally dissolved in a solvent with the solution of the chiral organozinc complex under an inert atmosphere at a temperature of about 0° C. to about 60° C. for about 1 hour to about 72 hours.

13. The process as recited in claim 12, wherein the first chiral additive has the formula:

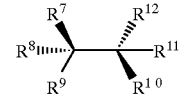

or its enantiomer or diastereomer, and the substituents are defined as:

$R^9$ and $R^{10}$ are independently:
OH, $NH_2$, $NHR^{17}$, $N(R^{17})_2$, or

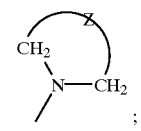

;

$R^7$, $R^8$, $R^{11}$ and $R^{12}$ are independently:
(a) H,
(b) $CF_3$,
(c) CN,
(d) $CONH_2$,
(e) CONH($C_1$–$C_6$-alkyl),
(f) CON($C_1$–$C_6$-alkyl)$_2$,
(g) $CO_2$—$C_1$–$C_6$-alkyl,
(h) $C_3$–$C_7$-cycloalkyl,
(i) $C_1$–$C_6$-alkyl, $C_2$–$C_6$-alkenyl, or $C_2$–$C_6$-alkynyl, unsubstituted or mono- or di-substituted with a substituent selected from the group consisting of: halo, $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, $CON(C_1-C_6\text{-alkyl})_2$, $NHCONH_2$, $NHCONH(C_1-C_6\text{-alkyl})$, $NHCON(C_1-C_6\text{-alkyl})_2$, $CO_2-C_1-C_6\text{-alkyl}$, $C_3-C_7\text{-cycloalkyl}$, $C_1-C_6\text{-alkoxy}$;

(j) $R^7$ and $R^8$ or $R^{11}$ and $R^{12}$ taken together can represent =O, forming a ketone, amide, acid or ester group;

(k)

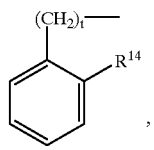

(k)

such that one and only one of $R^7$, $R^8$, $R^{11}$, or $R^{12}$ can bear this definition, except that at least one of the two carbons bearing $R^7$, $R^8$, $R^9$, $R^{10}$, $R^{11}$ and $R^{12}$ is a chiral center;

$R^9$ taken together with either $R^{11}$ or $R^{12}$ can represent:

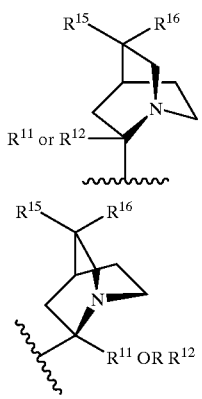

such that the other of $R^{11}$ or $R^{12}$ is hydrogen; or $R^{10}$ taken together with either $R^7$ or $R^8$ can represent:

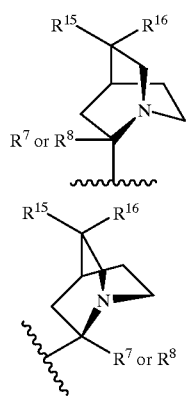

such that the other of $R^7$ or $R^8$ is hydrogen;

$R^{13}$ is: H, $C_1-C_6$-alkyl, or phenyl;

$R^{14}$ is: H, except that $R^7$ or $R^8$ and $R^{14}$ taken together can represent a carbon carbon bond, when t is 1 or 2 and $R^{11}$ or $R^{12}$ represents

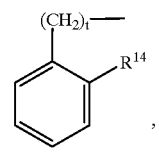

or $R^7$ or $R^8$ and $R^{14}$ taken together can represent $-(CH_2)_s-$, when t is 0 and $R^{11}$ or $R^{12}$ represents

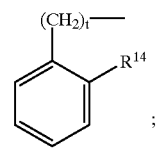

$R^{15}$ or $R^{16}$ is: $C_1-C_6$-alkyl, $C_2-C_6$-alkenyl, or $C_2-C_6$-alkynyl, unsubstituted or mono- or di-substituted with a substituent selected from the group consisting of: halo, $CF_3$, CN, $NO_2$, $NH_2$, $NH(C_1-C_6\text{-alkyl})$, $N(C_1-C_6\text{-alkyl})_2$, $CONH_2$, $CONH(C_1-C_6\text{-alkyl})$, $CON(C_1-C_6\text{-alkyl})_2$, $NHCONH_2$, $NHCONH(C_1-C_6\text{-alkyl})$, $NHCON(C_1-C_6\text{-alkyl})_2$, $CO_2-C_1-C_6\text{-alkyl}$, $C_3-C_7\text{-cycloalkyl}$, $C_1-C_6\text{-alkoxy}$; such that the other of $R^{15}$ and $R^{16}$ is hydrogen;

$R^{17}$ is: $C_1-C_6$-alkyl, unsubstituted or substituted with aryl, or aryl, wherein aryl is defined as phenyl or naphthyl;

Z represents:

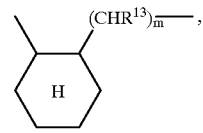

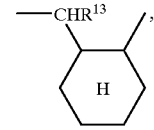

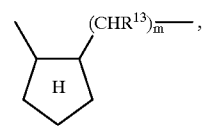

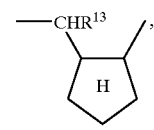

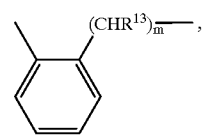

-continued

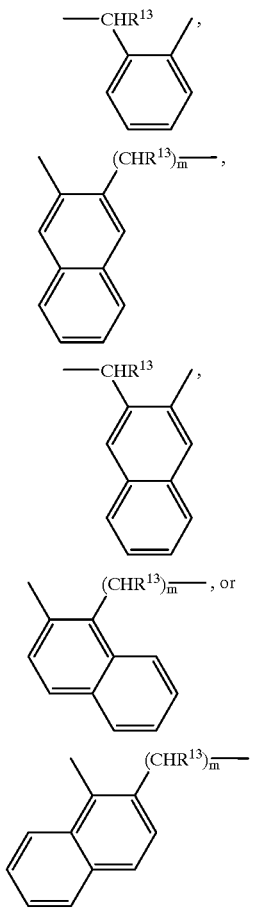

represents a six-membered ring, unsaturated or saturated, optionally substituted with one or two heteroatoms selected from N, O, or S, optionally substituted with $C_1$–$C_6$-alkyl;

represents: a five-membered ring, unsaturated or saturated, optionally substituted with one or two heteroatoms selected from N, O, or S, optionally substituted with $C_1$–$C_6$-alkyl;

n is 1, 2, or 3;
m is 0, or 1;
t is 0, 1, or 2; and
s is 1 or 2.

14. The process as recited in claim 13, wherein dialkylzinc is defined as a $[C_1$–$C_6$-alkyl$]_2$Zn.

15. The process as recited in claim 14, wherein the second additive is defined as: ROH, RSH, $RCO_2H$, $RSO_3H$, HX, $RCONH_2$, or arylNH$_2$; and R is $C_1$–$C_6$-alkyl, $C_2$–$C_6$-alkenyl, $C_2$–$C_6$-alkynyl, aryl, where aryl is defined as phenyl or naphthyl, and heteroaryl, where heteroaryl is defined as a 5 or 6-membered aromatic ring substituted with one or two heteroatoms selected from O, S, N, and each of which is unsubstituted or substituted with one, two or three substituents selected from the group consisting of: $NO_2$, Cl, Br, I, F, $CF_3$, $C_1$–$C_6$-alkyl, $C_1$–$C_6$-alkoxy, and N[$C_1$–$C_6$-alkyl]$_2$; and X is Cl, Br, I, or F.

16. The process as recited in claim 15, wherein the solvent is defined as a polar or non-polar aprotic solvent, or mixtures of said solvents.

17. The process as recited in claim 16, wherein the first chiral additive is selected from the group consisting of: (1R, 2S)-N-pyrrolidinyl norephedrine, N-methylephedrine, ephedrine, N,N-dibenzylnorephedrine, norephedrine, diethyl tartrate, pyrrolidine-methanol, (1R,2R)-pseudoephedrine, cinchonine, and (1S,2S)-N-methylpseudoephedrine.

18. The process as recited in claim 17, wherein the dialkylzinc is diethylzinc and dimethylzinc.

19. The process as recited in claim 18, wherein the second additive is defined as: MeOH, t-BuOH, $(CH_3)_3CCH_2OH$, $(CH_3)_3CCH(CH_3)OH$, $Ph_3COH$, $Cl_3CCH_2OH$, $F_3CCH_2OH$, $CH_2$=$CHCH_2OH$, $PhCH_2OH$, $(CH_3)_2NCH_2CH_2OH$, 4-$NO_2$-phenol, $CH_3CO_2H$, $CF_3CO_2H$, and $(CH_3)CCO_2H$.

20. The process as recited in claim 19, wherein the solvent is selected from the group consisting of: tetrahydrofuran, benzene, chlorobenzene, o-, m-, p-dichlorobenzene, dichloromethane, toluene, hexane, cyclohexane, pentane, methyl t-butyl ether, diethyl ether, N-methylpyrrolidine, or mixtures of said solvents.

21. The process as recited 20, wherein the organometallic reagent, $R^6M$, and $R^6$ represents: $C_2$–$C_6$-alkynyl; M represents: Li, or $MgX_1$; and $X_1$ represents: Cl, Br, I, F, or $CF_3SO_2$.

22. A process for the preparation of an amino alcohol of formula:

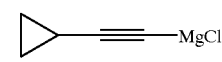

comprising the steps of:

a) adding slowly dimethylzinc or diethylzinc in toluene or neat to (1R, 2S)-N-pyrrolidinyl norephedrine in tetrahydrofuran under a nitrogen atmosphere at a temperature of about −20° C. to about 0° C. to form a chiral zinc complex;

b) adding an alcohol, where the alcohol is neopentyl alcohol or 2,2,2-trifluoroethanol, to the chiral zinc complex and heating to form an alcohol-containing chiral zinc complex;

c) mixing the alcohol-containing chiral zinc complex with

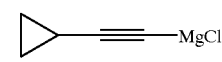

in tetrahydrofuran to form a chiral organozinc complex; and d) mixing a ketone of formula:

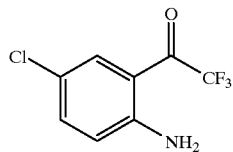

with the solution of the chiral organozinc complex under an inert atmosphere at a temperature of about 0° C. to about 20° C. for about 2 hours to about 48 hours to give the amino alcohol.

23. A process for the preparation of an amino alcohol of formula:

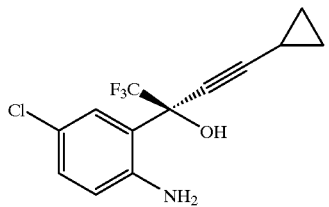

comprising the steps of:
a) adding slowly dimethylzinc or diethylzinc in toluene or neat to (1R, 2S)-N-pyrrolidinyl norephedrine and an alcohol, where the alcohol is neopentyl alcohol or 2,2,2-trifluoroethanol, in tetrahydrofuran under a nitrogen atmosphere at a temperature of about −20° C. to about 0° C. to form an alcohol containing chiral zinc complex;

b) mixing the alcohol-containing chiral zinc complex with

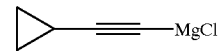

in tetrahydrofuran to form a chiral organozinc complex; and c) mixing a ketone of formula:

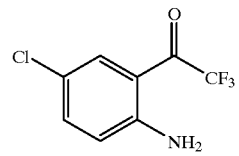

with the solution of the chiral organozinc complex under an inert atmosphere at a temperature of about 0° C. to about 20° C. for about 2 hours to about 48 hours to give the amino alcohol.

* * * * *

UNITED STATES PATENT AND TRADEMARK OFFICE
CERTIFICATE OF CORRECTION

PATENT NO. : 6,015,926
DATED : January 18, 2000
INVENTOR(S) : Cheng Yi Chen, Lushi Tan, Richard D. Tillyer It is certified that error appears in the above-identified patent and that said Letters Patent is hereby corrected as shown below:

Column 7,
Line 55, before "taken together", replace "$R^9$" with -- $R^{10}$ --.

Column 8,
Line 1, before "taken together", replace "$R^{10}$" with -- $R^9$ --.

Column 12,
Line 15, before "taken together", replace "$R^9$" with -- $R^{10}$ --.
Line 28, before "taken together", replace "$R^{10}$" with -- $R^9$ --.

Column 41, claim 4,
Line 14, before "taken together", replace "$R^9$" with -- $R^{10}$ --.
Line 27, before "taken together", replace "$R^{10}$" with -- $R^9$ --.

Column 43, claim 8,
Lines 16 and 17, delete "pyrrolidine-methanol" and "cinchonine" respectively.

Column 45, claim 13,
Line 24, before "taken together", replace "$R^9$" with -- $R^{10}$ --.
Line 44, "taken together", replace "$R^{10}$" with -- $R^9$ --.

Column 48, claim 17,
Lines 15 and 16, delete "pyrrolidine-methanol" and "cinchonine" respectively.

Signed and Sealed this

Twenty-fifth Day of December, 2001

Attest:

*Attesting Officer*

JAMES E. ROGAN
*Director of the United States Patent and Trademark Office*